(12) United States Patent
Ortiz

(10) Patent No.: US 7,591,828 B2
(45) Date of Patent: Sep. 22, 2009

(54) RESPOSABLE ANASTOMOTIC RING APPLIER DEVICE

(75) Inventor: Mark S. Ortiz, Milford, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 567 days.

(21) Appl. No.: 11/187,083

(22) Filed: Jul. 22, 2005

(65) Prior Publication Data

US 2007/0021757 A1 Jan. 25, 2007

(51) Int. Cl.
*A61B 17/08* (2006.01)
(52) U.S. Cl. .................................... 606/153
(58) Field of Classification Search ........... 606/139, 606/153–156
See application file for complete search history.

(56) References Cited

U.S. PATENT DOCUMENTS

| | | | |
|---|---|---|---|
| 5,855,312 A | | 1/1999 | Toledano |
| 6,068,636 A | * | 5/2000 | Chen .......................... 606/153 |
| 6,171,321 B1 | * | 1/2001 | Gifford et al. ................ 606/153 |
| 6,451,029 B1 | * | 9/2002 | Yeatman ...................... 606/139 |
| 6,485,496 B1 | * | 11/2002 | Suyker et al. ................ 606/153 |
| 7,195,142 B2 | * | 3/2007 | Orban, III ................. 227/176.1 |
| 2003/0032967 A1 | * | 2/2003 | Park et al. .................... 606/153 |
| 2003/0120292 A1 | * | 6/2003 | Park et al. .................... 606/153 |
| 2004/0102796 A1 | * | 5/2004 | Hill et al. ..................... 606/153 |
| 2006/0253039 A1 | * | 11/2006 | McKenna et al. ............ 600/486 |

FOREIGN PATENT DOCUMENTS

EP 0564783 2/1993

OTHER PUBLICATIONS

Office Action dated Jan. 4, 2006, for U.S. Appl. No. 10/675,497, filed Sep. 30, 2003.
European Search Report, dated Oct. 30, 2006, for EP Application No. 06253839.2.

* cited by examiner

*Primary Examiner*—(Jackie) Tan-Uyen T. Ho
*Assistant Examiner*—Gregory A Anderson
(74) *Attorney, Agent, or Firm*—Frost Brown Todd LLC

(57) ABSTRACT

A surgical instrument that is operable to deploy an anastomotic ring device comprises a proximal portion and a distal portion. The distal portion comprises a ring deployment mechanism, which is configured to receive and deploy an anastomotic ring. The proximal portion comprises a mechanism that is operable to remotely actuate the ring deployment mechanism. The distal portion is removable from the proximal portion. The distal portion may be selectively engaged with the proximal portion by a series of annular flanges and clamp arms that are configured to engage the annular flanges. The ability to remove the distal portion of the instrument permits the replacement of the ring deployment mechanism without requiring the replacement of the instrument in its entirety.

13 Claims, 22 Drawing Sheets

RESPOSABLE ANASTOMOTIC RING APPLIER DEVICE

FIELD OF THE INVENTION

The present invention relates, in general, to surgery and, more particularly, to a device for performing a surgical procedure on the digestive system.

BACKGROUND OF THE INVENTION

The percentage of the world population suffering from morbid obesity is steadily increasing. Severely obese persons may be susceptible to increased risk of heart disease, stroke, diabetes, pulmonary disease, and accidents. Because of the effects of morbid obesity on the life of the patient, methods of treating morbid obesity have been the subject of intense research.

One known method for treating morbid obesity includes the use of anastomotic rings. Devices for applying anastomotic rings are known in the art. Devices of this nature are commonly adapted to insert a compressed anastomotic ring to an anastomotic opening formed between proximate gastrointestinal tissue walls. These applier devices may utilize a ring deployment mechanism comprising an expansion element that is actuated once the compressed ring is placed in the anastomotic opening, causing the anastomotic ring to expand from its compressed, cylindrically-shaped position to an actuated, hollow rivet-shaped position.

It may be desirable to have an applier device that has one or more removable portions. For instance, it may be desirable to have an applier with a ring deployment mechanism that can be separated from the rest of the applier device, such as the handle. Such removability or separability may be desirable for a variety of purposes. By way of example only, a handle portion of an applier device may be reusable, while the ring deployment mechanism of the applier device is disposable. In other words, by configuring the applier device such that the ring deployment mechanism is removable, the ring deployment mechanism may be replaced in lieu of replacing the applier device in its entirety. As another merely illustrative example, various distal ends of applier devices may be modular, such that the same handle may be used with various types of distal ends. Other advantages that may result from having an applier device with one or more removable parts will be apparent to those of ordinary skill in the art.

BRIEF SUMMARY OF THE INVENTION

Several embodiments of the present invention provide an anastomotic ring applier device that allows the replacement of a distal portion of the device while keeping the proximal portion of the device.

In one embodiment, a surgical instrument for deploying an anastomotic ring device at an anastomosis site comprises a distal portion and a proximal portion. The distal portion comprises a ring deployment mechanism. The ring deployment mechanism is configured to receive and deploy an anastomotic ring. The proximal portion is in communication with the distal portion. The proximal portion comprises one or more actuation members operable to actuate at least a portion of the ring deployment mechanism. The distal portion is selectively removable from the proximal portion.

In another embodiment, a surgical instrument is operable to deploy an anastomotic ring device at an anastomosis site. The instrument comprises an actuating member configured to receive an anastomotic ring. The actuating member is moveable between a cylindrical, unactuated position and a hollow rivet forming position in response to at least one actuating force. The instrument further comprises a handle including an actuating mechanism that is operable to produce the at least one actuating force. The instrument further comprises an elongate shaft connecting the handle to the actuating member. The shaft is configured to transfer the at least one actuating force from the handle to the actuating member. The elongate shaft comprises a first portion and a second portion. At least a portion of the first portion of the shaft is adjacent to the actuating member. At least a portion of the second portion of the shaft is adjacent to the handle. The first portion of the shaft is configured to selectively couple with the second portion of the shaft.

In yet another embodiment, a surgical instrument is operable to deploy an anastomotic attachment device at an anastomosis site. The instrument comprises a deploying means for deploying an anastomotic attachment device in response to one or more actuating forces. The instrument further comprises an actuating means for providing the one or more actuating forces. The instrument further comprises a coupling means for selectively coupling and decoupling the deploying means with the actuating means.

More embodiments will be described below. Other embodiments will be apparent to those of ordinary skill in the art.

BRIEF DESCRIPTION OF THE FIGURES

The accompanying drawings, which are incorporated in and constitute a part of this specification, illustrate versions of the invention, and, together with the general description of the invention given above, and the detailed description of the versions given below, serve to explain the principles of the present invention.

DETAILED DESCRIPTION OF EMBODIMENTS OF THE INVENTION

Figure 1:
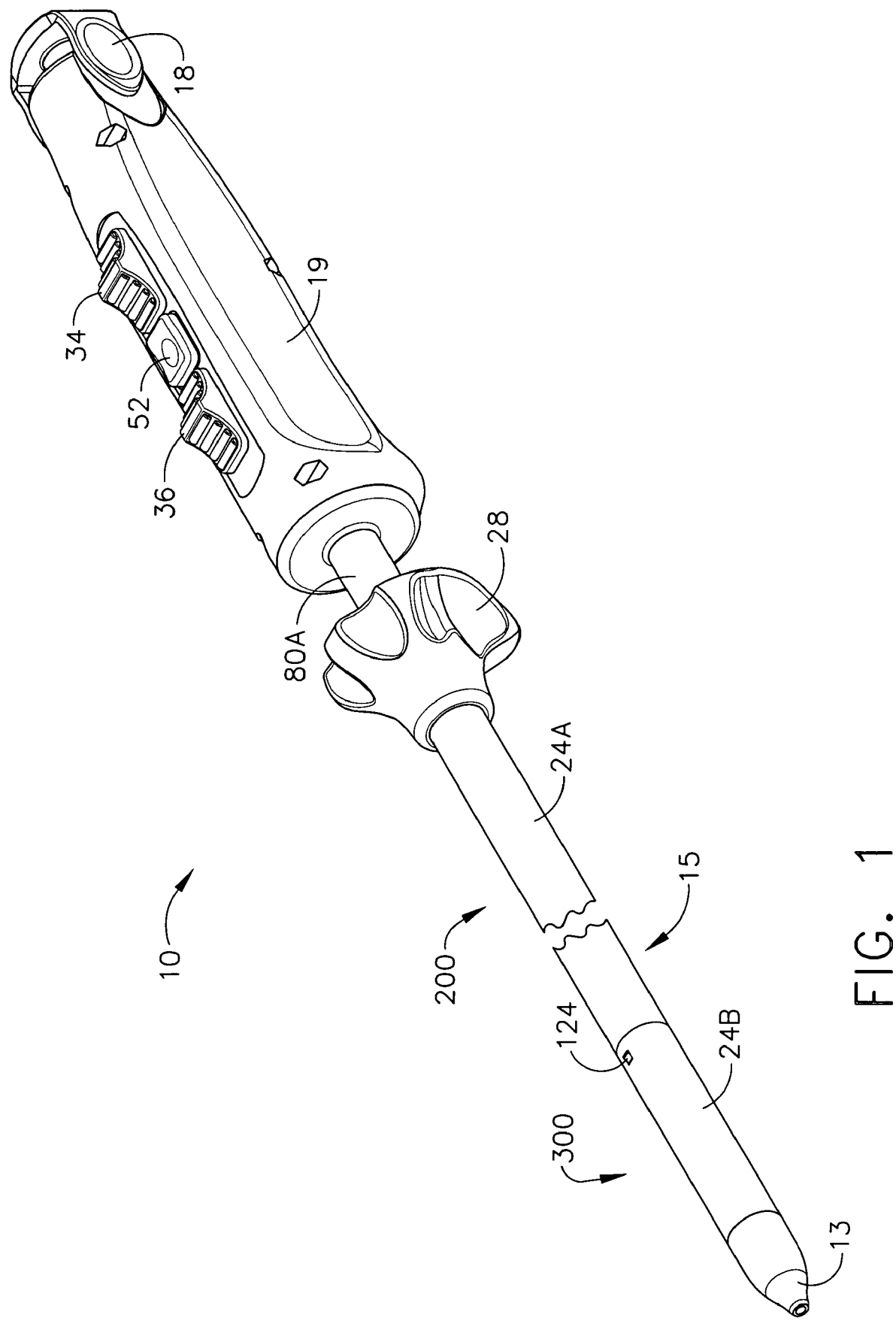
FIG. 1 is a perspective view of an anastomotic ring applier device, shown with a retracted tip.
Figure 2:
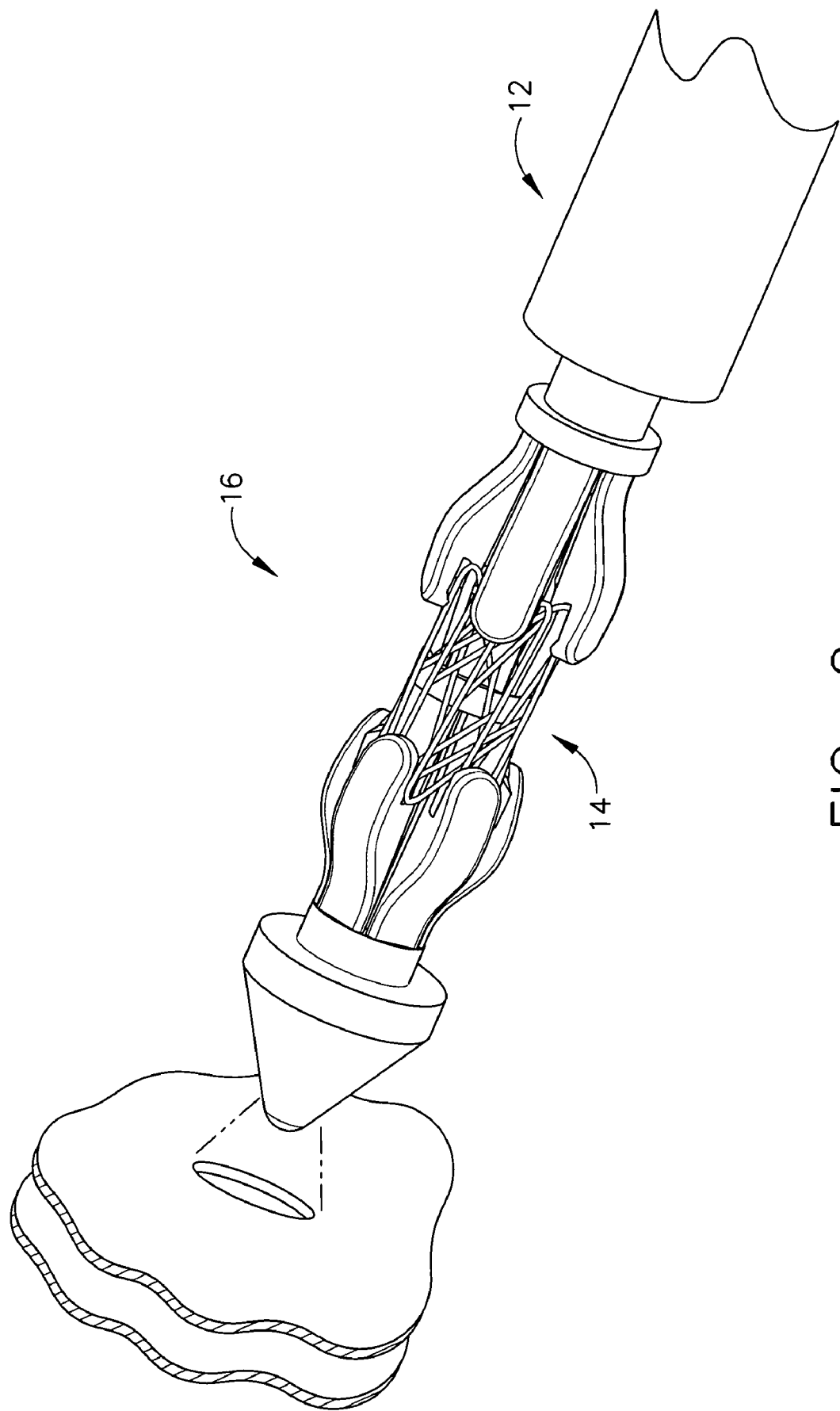
FIG. 2 is a partial perspective view of the distal portion of an anastomotic ring applier device holding an anastomotic ring in an unactuated position.
Figure 3:
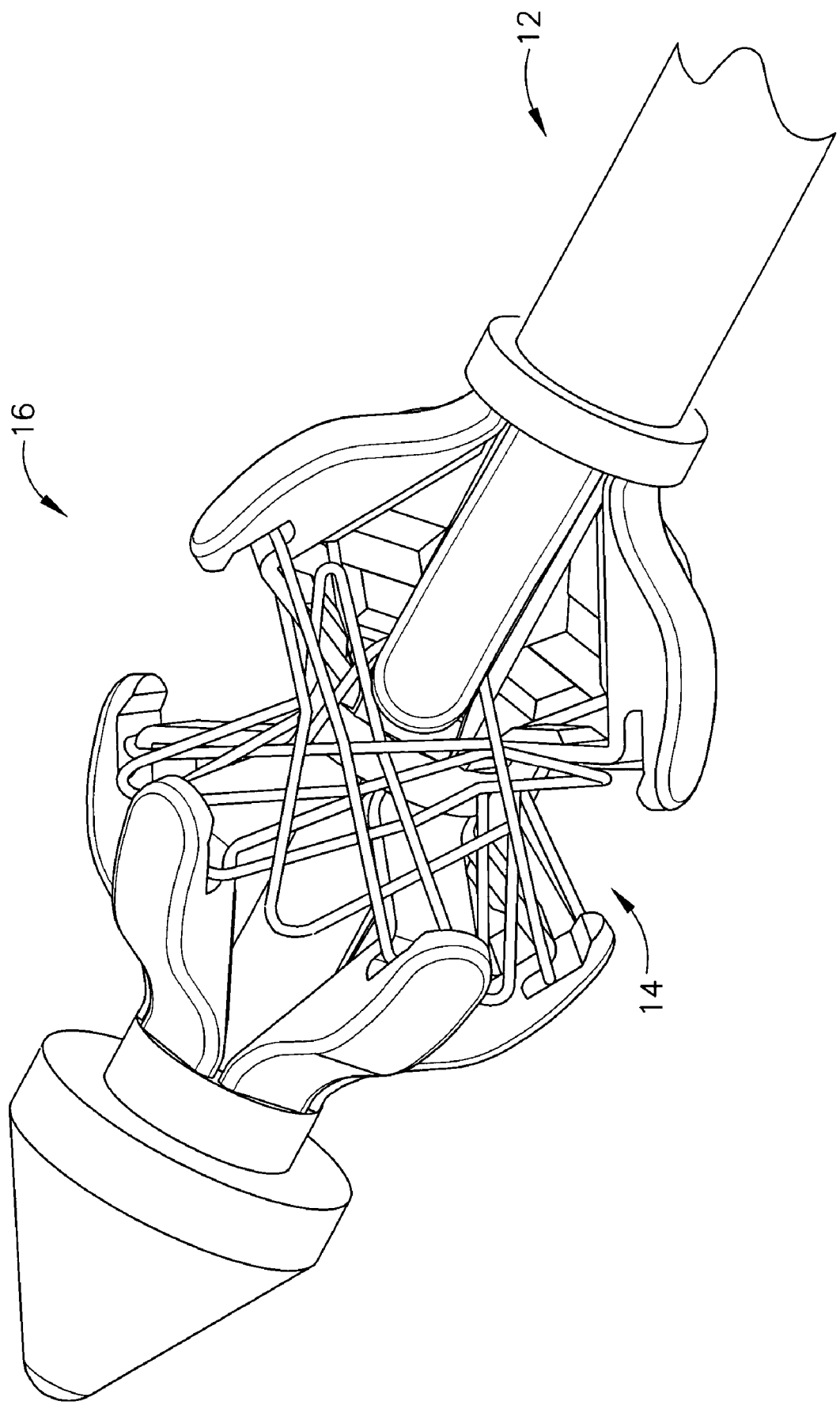
FIG. 3 is a partial perspective view of the distal portion of the device of FIG. 2 holding an anastomotic ring in the actuated position.
Figure 4:
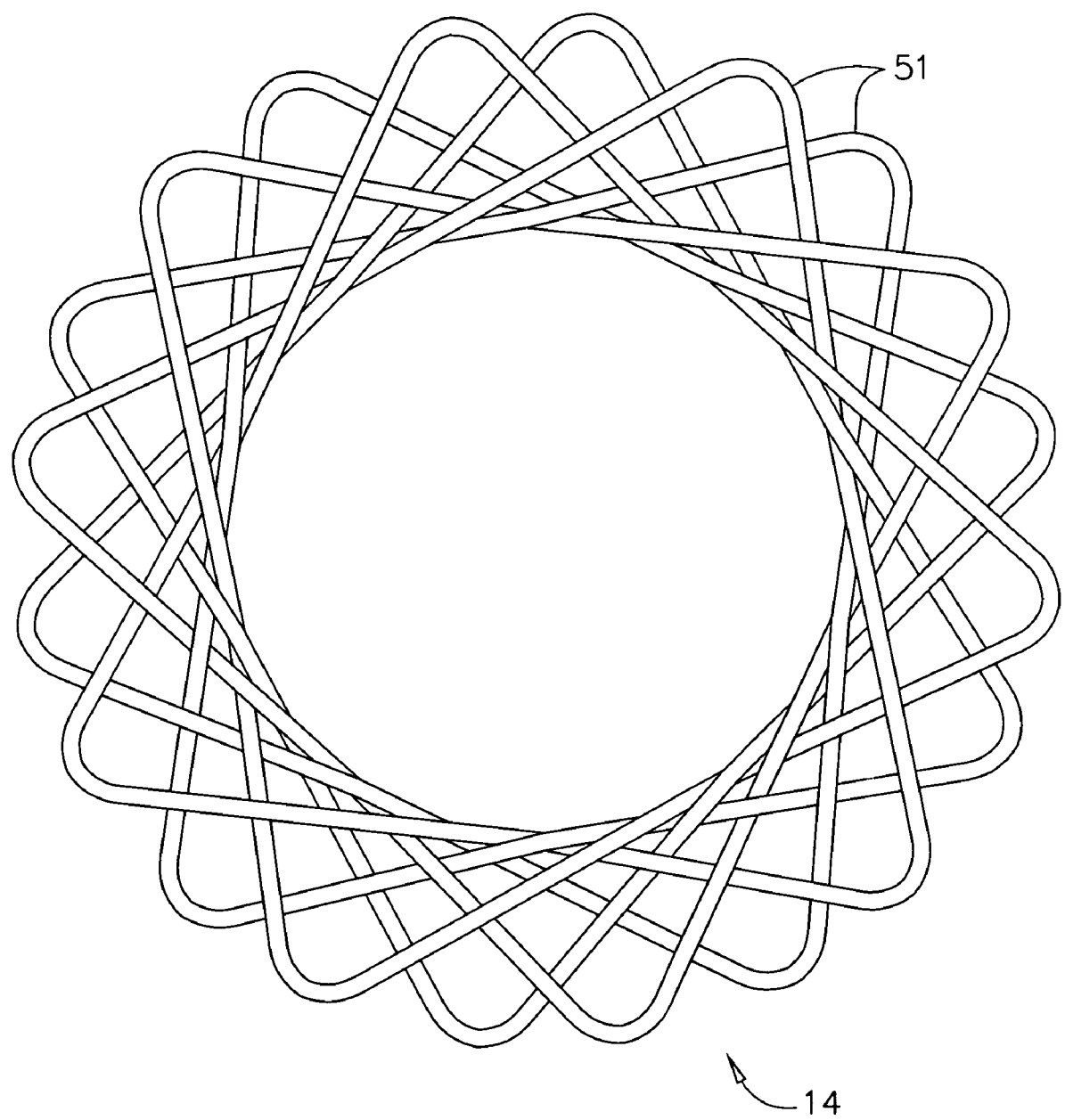
FIG. 4 is a frontal view of an actuated anastomotic ring.

Turning to the Drawings, wherein like numerals denote like components throughout the several views, FIG. 1 depicts an applier 10 that is operable to deploy and actuate an anastomotic ring device (not pictured in FIG. 1) from a generally cylindrical shape to one having properties of a hollow rivet, or ring, capable of forming an anastomotic attachment at an anastomosis target site, such as in a bariatric gastric bypass of a morbidly obese patient. FIG. 2 depicts another applier 12. It will be appreciated that appliers 10, 12 may be used in a variety of ways, including but not limited to laparoscopically or endoscopically. Applier 12 is shown in FIG. 2 with an anastomotic ring 14 on a deployment mechanism 16. In FIG. 2, anastomotic ring 14 is shown in the compressed, cylindrically-shaped position. In FIG. 3, deployment mechanism 16 of applier 12 has moved anastomotic ring 14 to the actuated, hollow rivet-shaped position. FIG. 4 is a close-up view of anastomotic ring 14 in the actuated position. Anastomotic ring 14 may comprise a shape memory effect (SME) material, such as nitinol by way of example only, that further assists in actuation to an engaging hollow rivet shape. Other suitable anastomotic ring 14 materials will be apparent to those of ordinary skill in the art. An exemplary anastomotic ring 14 is described in detail in U.S. Patent Application Publ. No. US 2003/0032967 to Park et al.

It will be appreciated that the terms "proximal" and "distal" are used herein with reference to a clinician gripping a handle of applier 10. It will be further appreciated that for convenience and clarity, spatial terms such as "right", "left", "vertical" and "horizontal" are used herein with respect to the drawings. However, surgical instruments are used in many orientations and positions, and these terms are not intended to be limiting and absolute. In addition, aspects of the invention have application to surgical procedures performed endoscopically and laparoscopically, as well as an open procedure or other procedures. Use herein of one of these or similar terms should not be construed to limit the present invention for use in only one category of surgical procedure.

Figure 13:
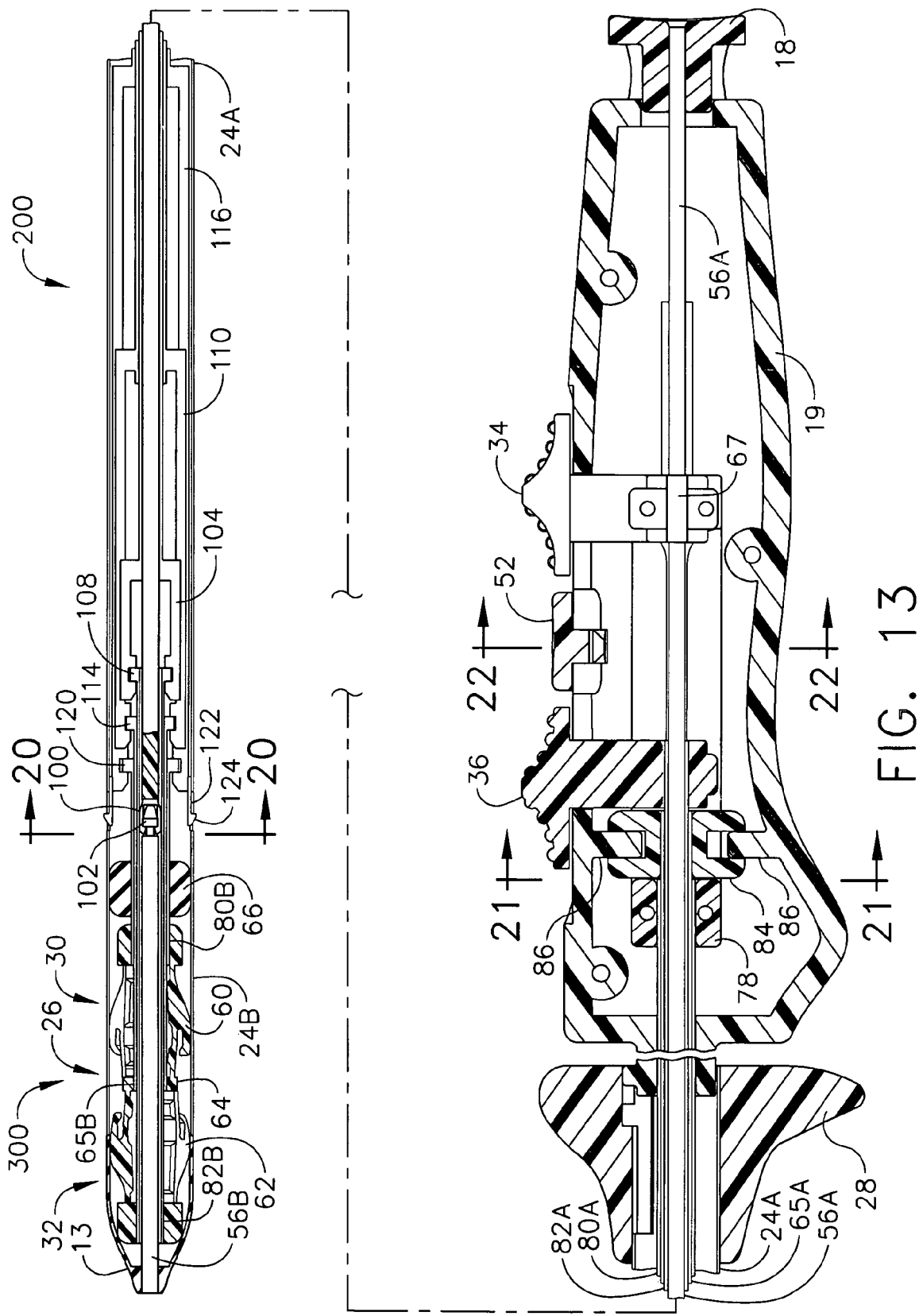
FIG. 13 is a partial cross-sectional view of the device of FIG. 1, shown with a retracted tip.

As shown in FIGS. 1 and 5-10, applier 10 of the present example includes a tip actuator 18 located on a handle 19. Tip actuator 18 is operable to move tip 13 from a retracted position to an extended position. Applier 10 of the present example also has a shaft 15 comprising a proximal sheath portion 24A and a distal sheath portion 24B (proximal and distal sheath portions referred to collectively as "sheath"). Sheath 24A, 24B is moveable from a first position to a second position. In the first position, sheath 24A, 24B is configured such that distal sheath portion 24B selectively covers a portion of ring deployment mechanism 26 (FIGS. 1 and 13) to prevent tissue from catching on ring deployment mechanism 26 during insertion and extraction of applier 10. Applier 10 further comprises a sheath actuator 28 operable to move sheath 24A, 24B between the first and second positions. As shown, tip 13 is also configured to selectively cover a portion of ring deployment mechanism 26. Sheath 24A, 24B and tip 13 are configured such that deployment mechanism 26 is exposed and free to actuate when sheath 24A, 24B is in the second position and tip is in the extended position. Suitable alternatives to sheath 24A, 24B, sheath actuator 28, tip 13, and/or tip actuator 18 will be apparent to those of ordinary skill in the art.

Figure 6:
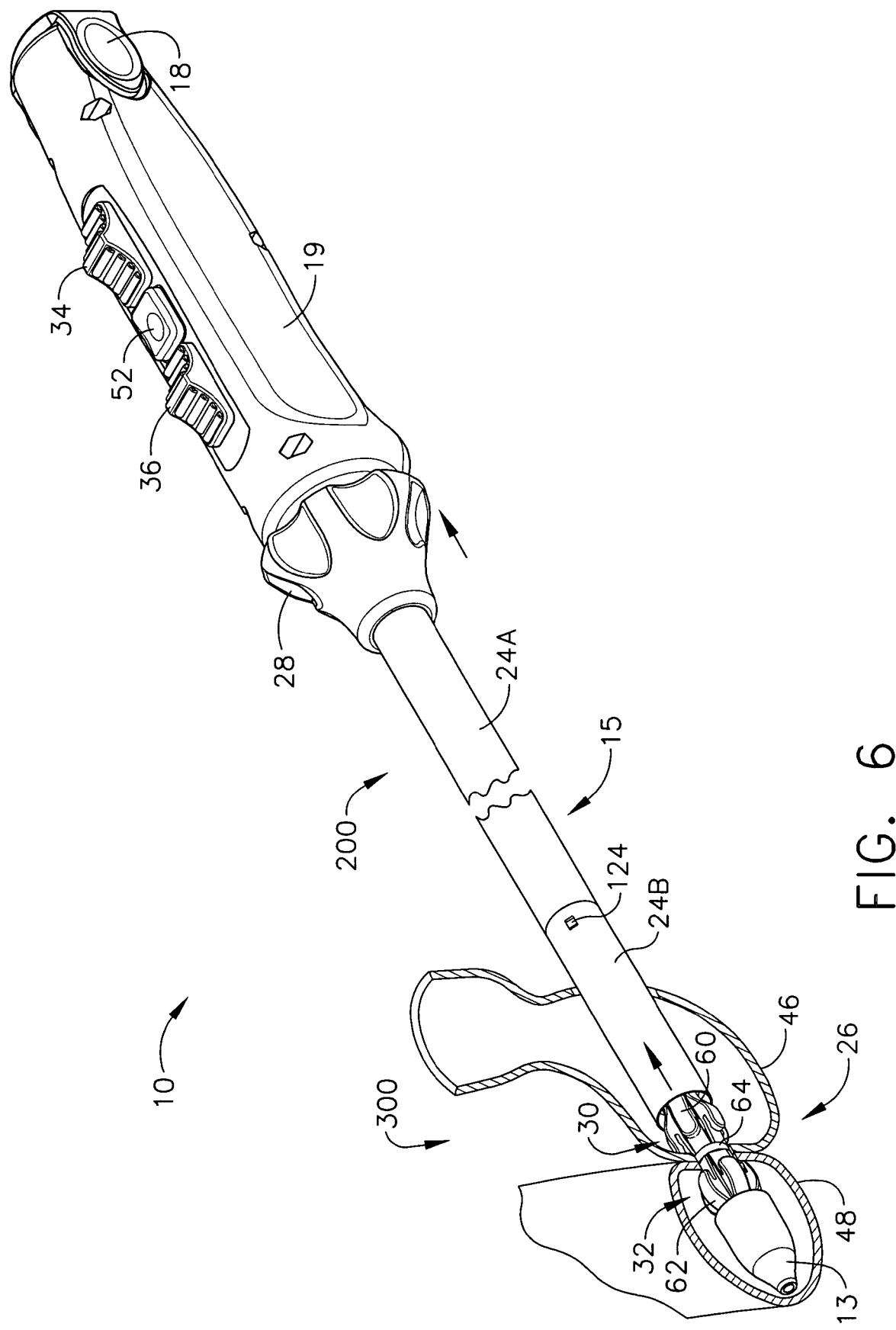
FIG. 6 is a perspective view of the device of FIG. 1, shown with the sheath retracted.
Figure 7:
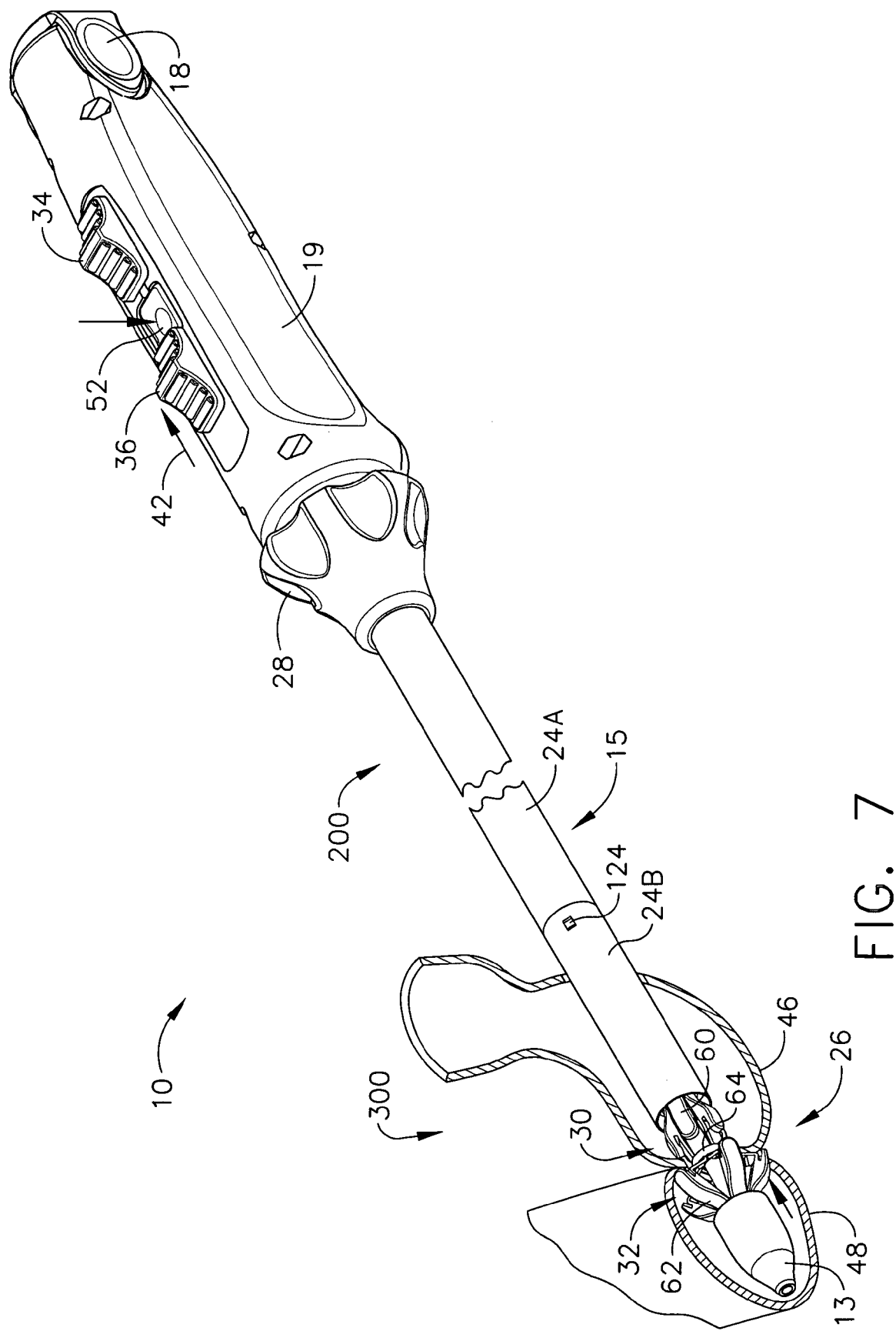
FIG. 7 is a perspective view of the device of FIG. 1, shown with a distal portion of the ring deployment mechanism partially actuated.
Figure 8:
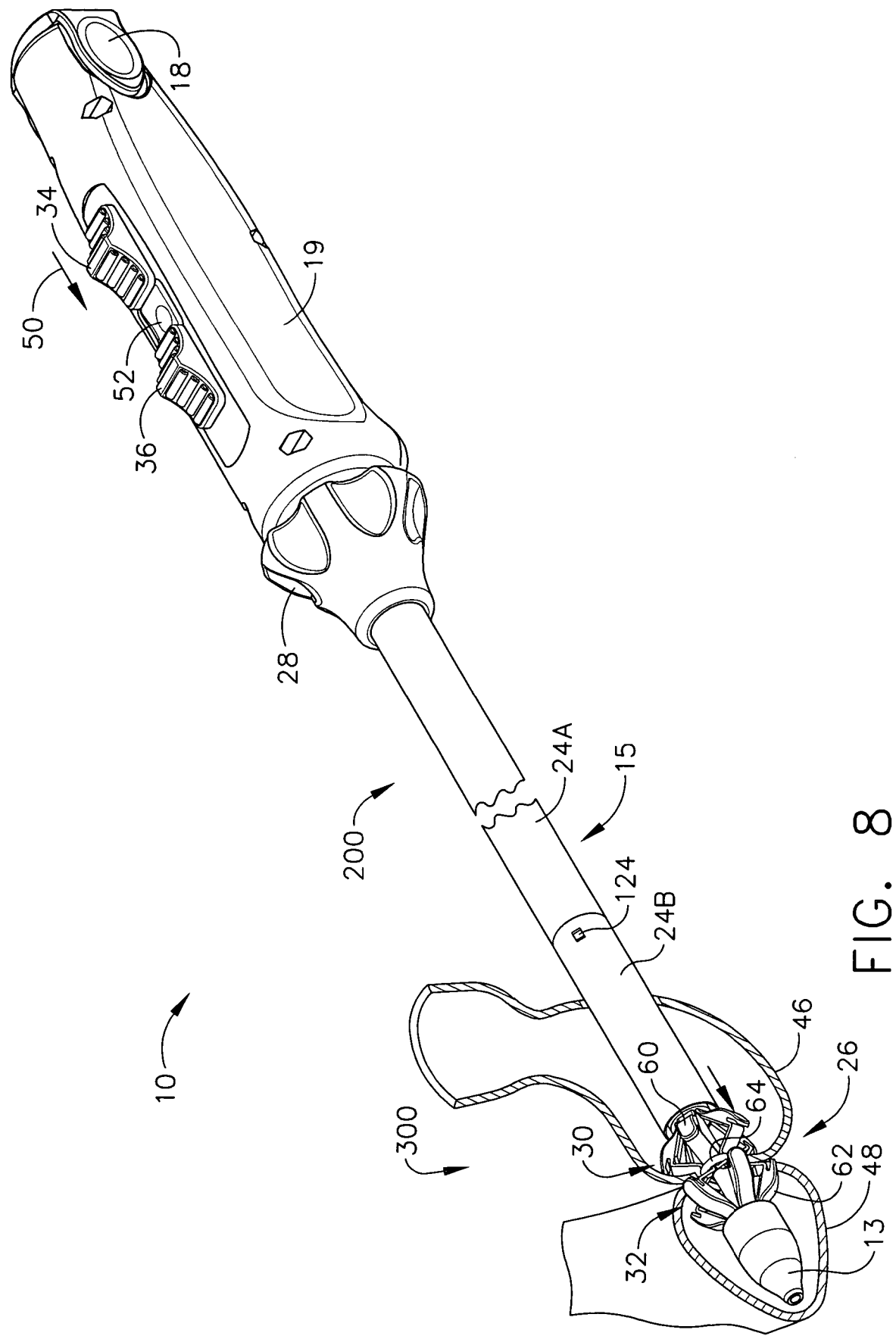
FIG. 8 is a perspective view of the device of FIG. 1, shown with both a distal portion and a proximal portion of the ring deployment mechanism partially actuated.
Figure 9:
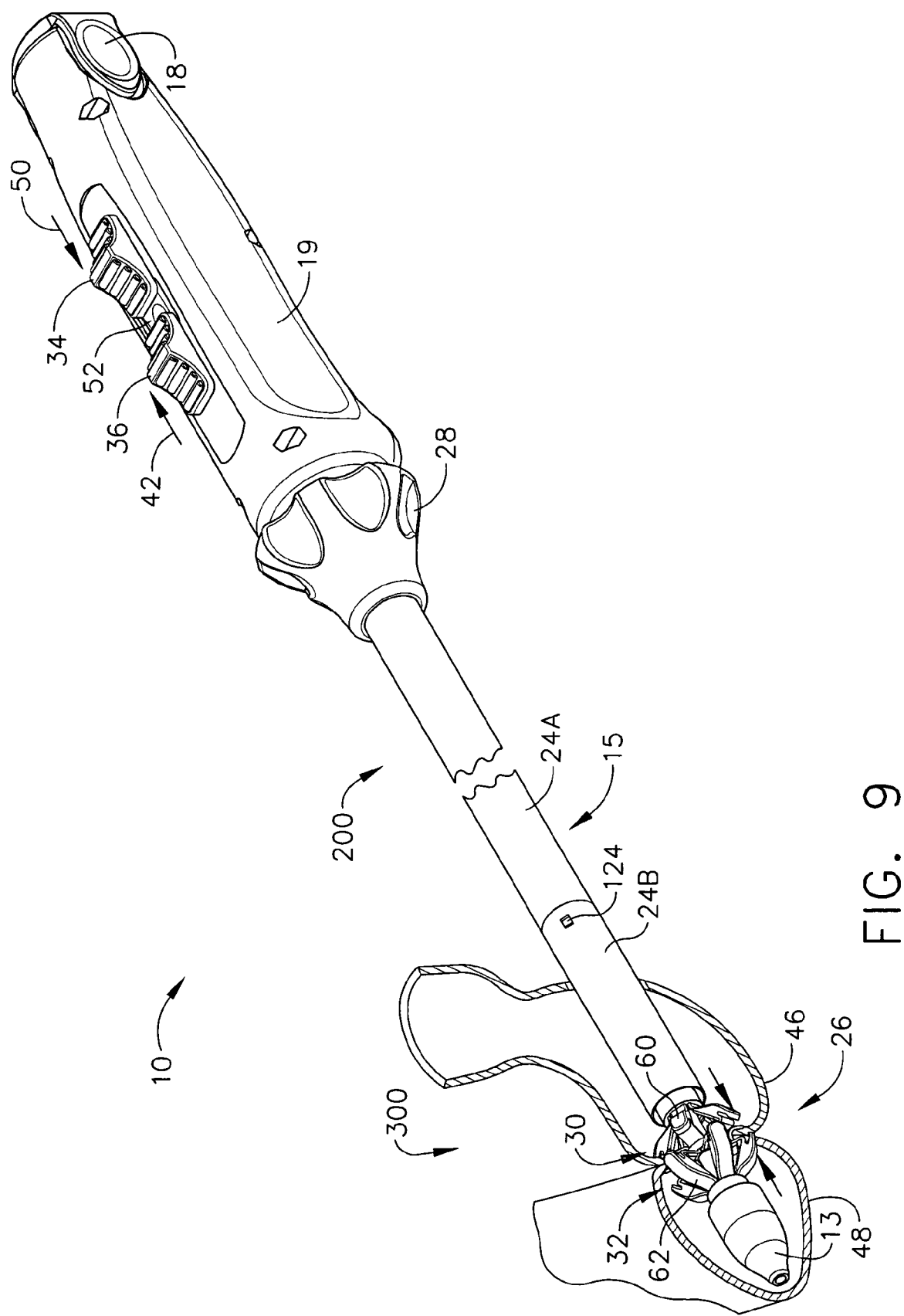
FIG. 9 is a perspective view of the device of FIG. 1, shown with both a distal portion and a proximal portion of the ring deployment mechanism fully actuated.
Figure 15:
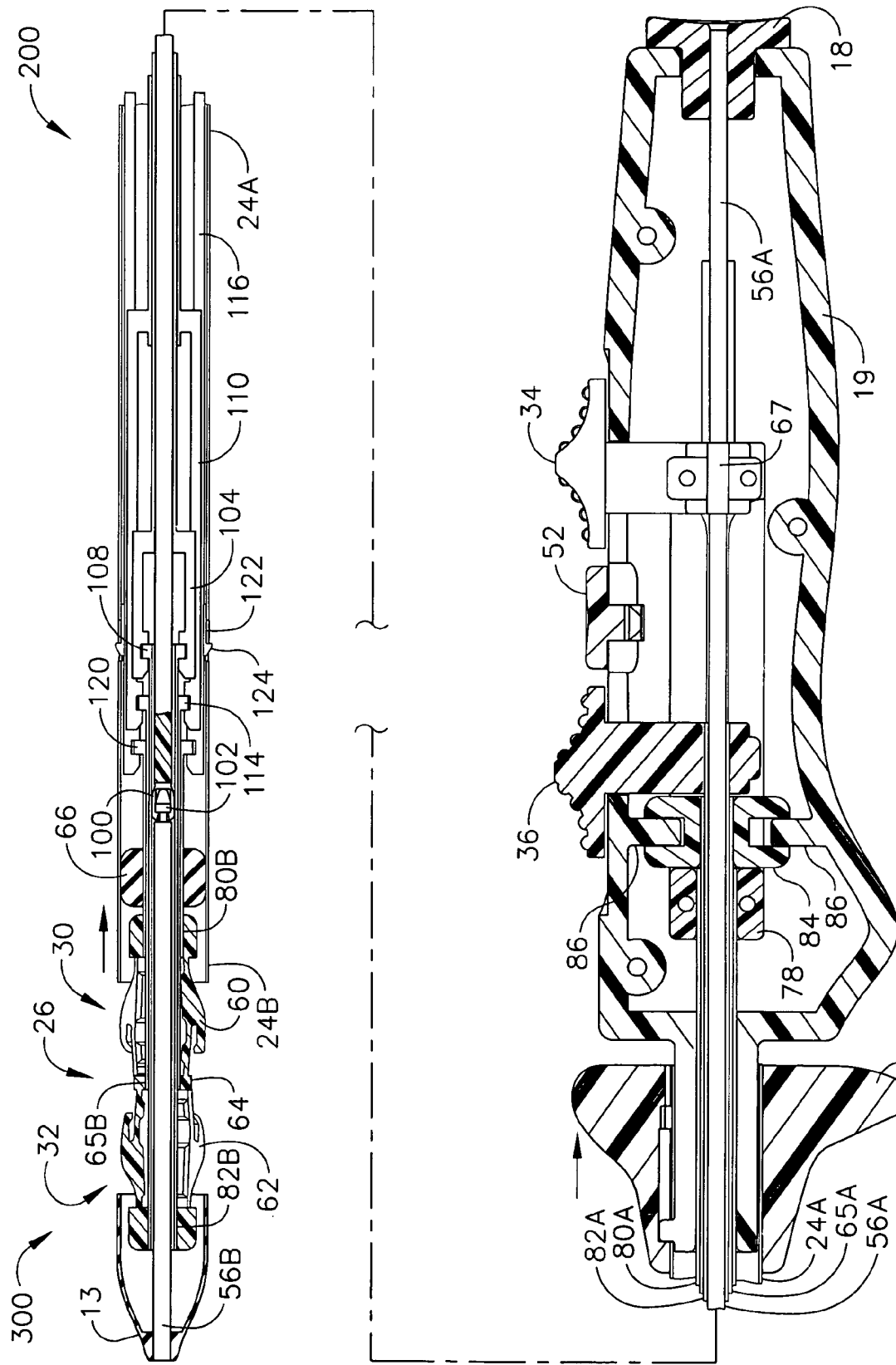
FIG. 15 is a partial cross-sectional view of the device of FIG. 1, shown with the sheath retracted.
Figure 16:
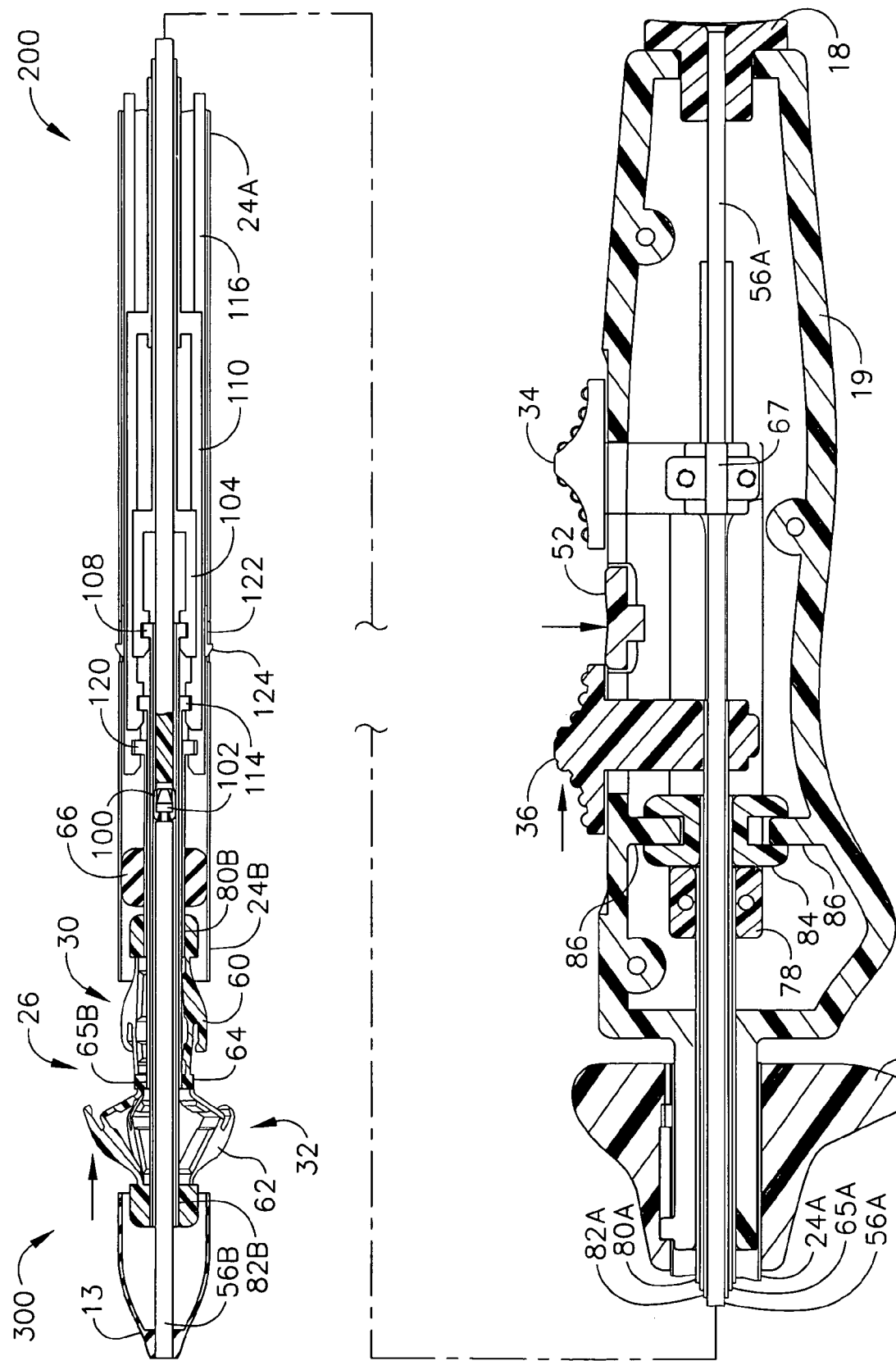
FIG. 16 is a partial cross-sectional view of the device of FIG. 1, shown with a distal portion of the ring deployment mechanism partially actuated.
Figure 17:
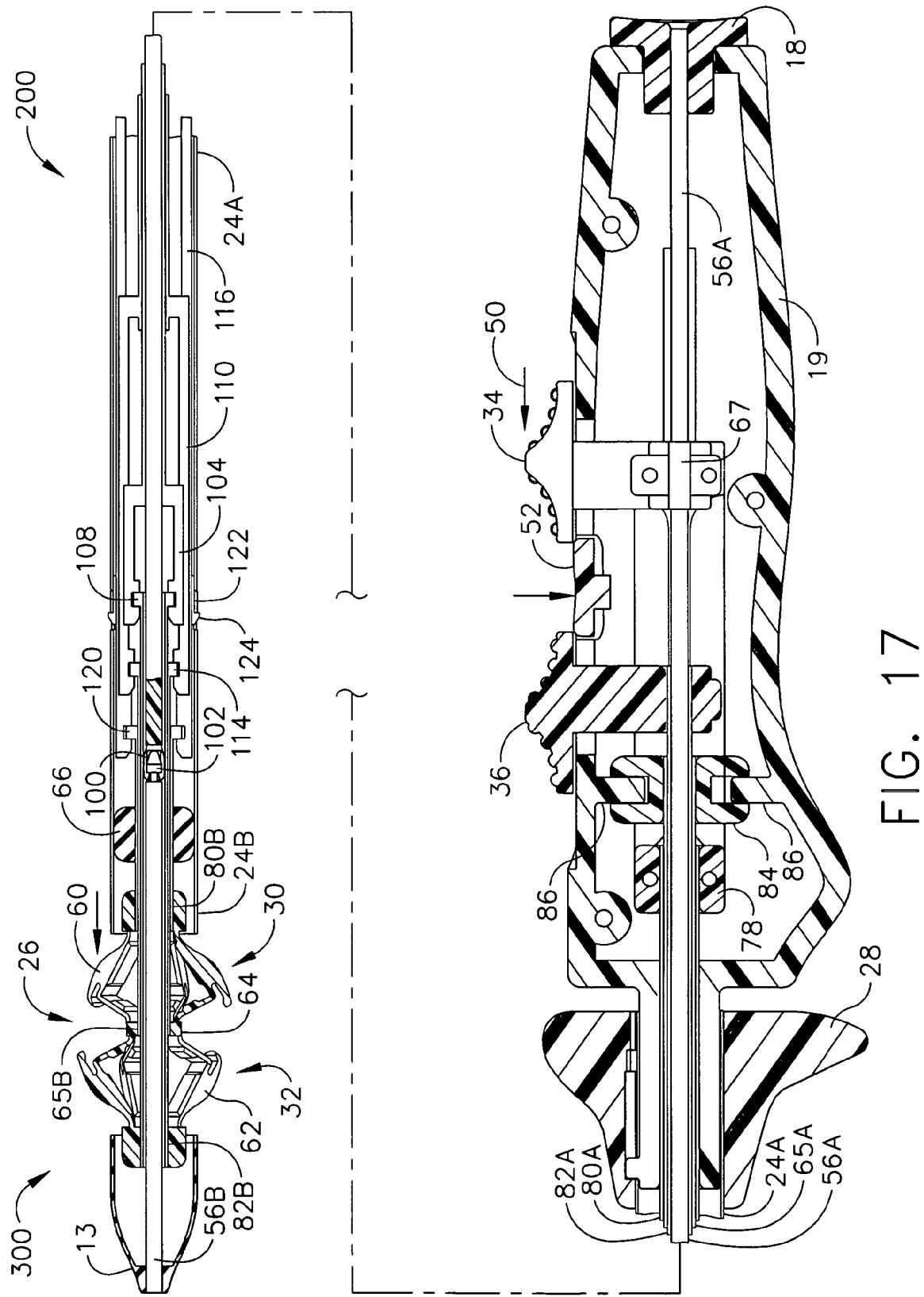
FIG. 17 is a partial cross-sectional view of the device of FIG. 1, shown with both a distal portion and a proximal portion of the ring deployment mechanism partially actuated.
Figure 18:
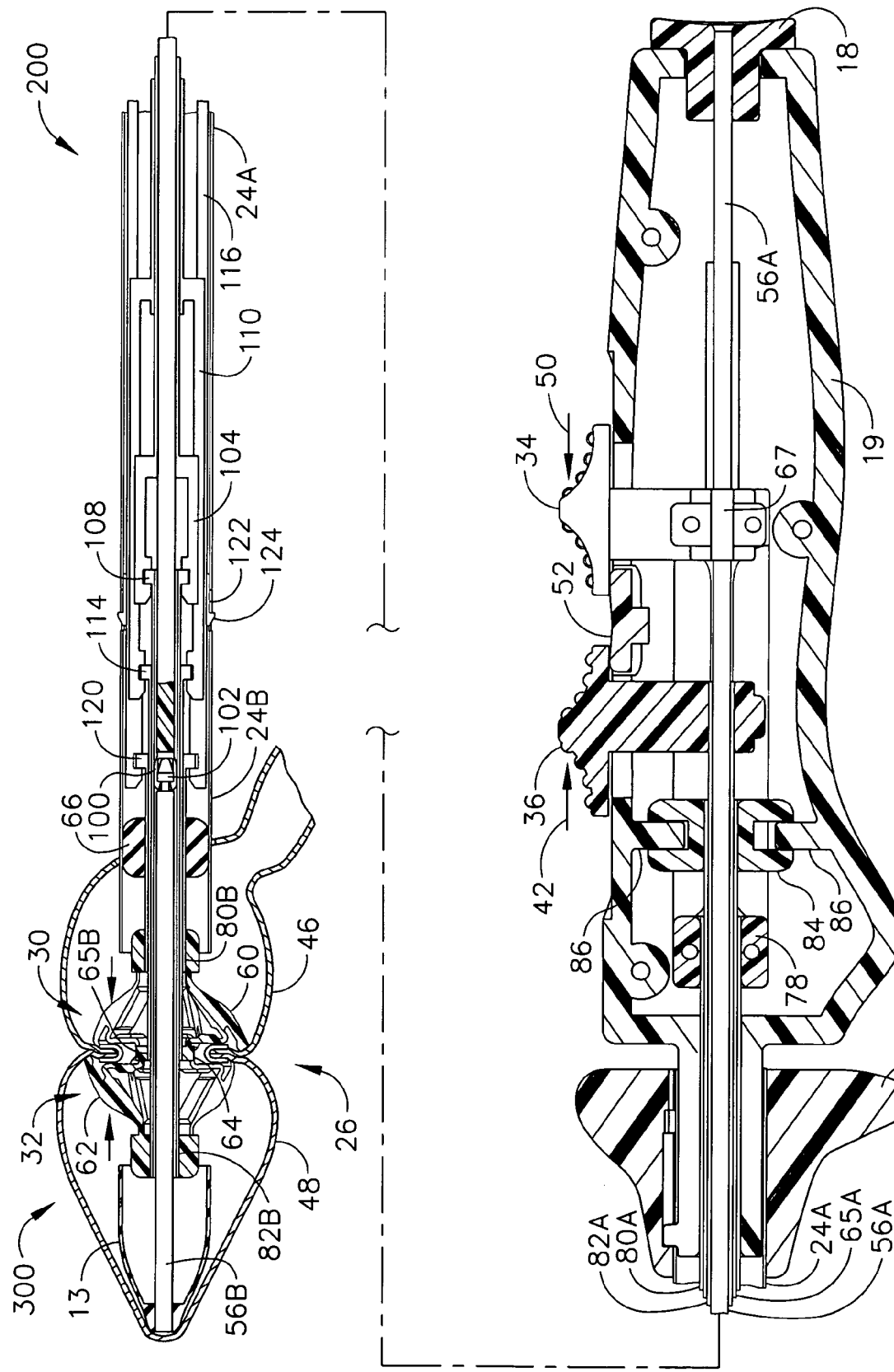
FIG. 18 is a partial cross-sectional view of the device of FIG. 1 disposed in an anastomotic opening, shown with both a distal portion and a proximal portion of the ring deployment mechanism fully actuated.

Referring now to FIGS. 6-11 and 13-19, ring deployment mechanism 26 of the present example comprises a proximal portion 30 and a distal portion 32. Applier 10 further comprises a pair of deployment actuators 34, 36. As described in more detail below, first deployment actuator 34 is operable to actuate proximal portion 30 of ring deployment mechanism 26; and second deployment actuator 36 is operable to actuate distal portion 32. In FIGS. 7 and 16, distal portion 32 is shown in a partially actuated position for partially deploying a distal portion of an anastomotic ring 14. Arrow 42 depicts actuating motion of second actuator 36. In FIGS. 8 and 17, proximal portion 30 is shown in a partially actuated position for partially deploying a proximal portion of anastomotic ring 14 to partially complete an anastomotic attachment between proximate tissue walls 46, 48. Arrow 50 depicts the actuating motion of first actuator 34. FIGS. 9 and 18 show distal portion 32 and proximal portion 30 each in a fully actuated position. It will be appreciated that proximal portion 30 may be actuated before distal portion 32, or that proximal portion 30 and distal portion 32 may be actuated concomitantly.

In the present example, proximal portion 30 of ring deployment mechanism 26 comprises a plurality of fingers 60; and distal portion 32 also comprises a plurality of fingers 62. Fingers 60, 62 are configured to hold an anastomotic ring 14 by engaging petals 51 prior to and during deployment of the anastomotic ring 14, and release petals 51 upon deployment of the anastomotic ring 14. Both proximal fingers 60 and distal fingers 62 are in a double-hinged relationship with a stationary mid-ring 64 of ring deployment mechanism 26. Proximal fingers 60 are configured to slide toward mid-ring 64 in response to engagement of first actuator 34, causing proximal fingers 60 to actuate outwardly from shaft 15. Mid-ring 64 is held stationary by a stationary distal ground tube portion 65B. Likewise, distal fingers 62 are configured to slide toward mid-ring 64 in response to actuation of second actuator 36, causing distal fingers 62 to actuate outwardly from shaft 15. As shown in FIGS. 11, and 13-19, and as will be described in greater detail below, the above-described actuating components of ring deployment mechanism comprise a series of concentric distal tube portions 82B, 65B, 80B within shaft 15. A bushing 66 is included within shaft 15 to keep the concentric distal tube portions 82B, 65B, 80B centered. It will be appreciated, however, that the above-described components need not be concentrically aligned, and that any suitable alternative to bushing 66 may be used. It will also be appreciated that any suitable alternative(s) to ring deployment mechanism 26 and/or deployment actuators 34, 36 may be used.

Figure 14:
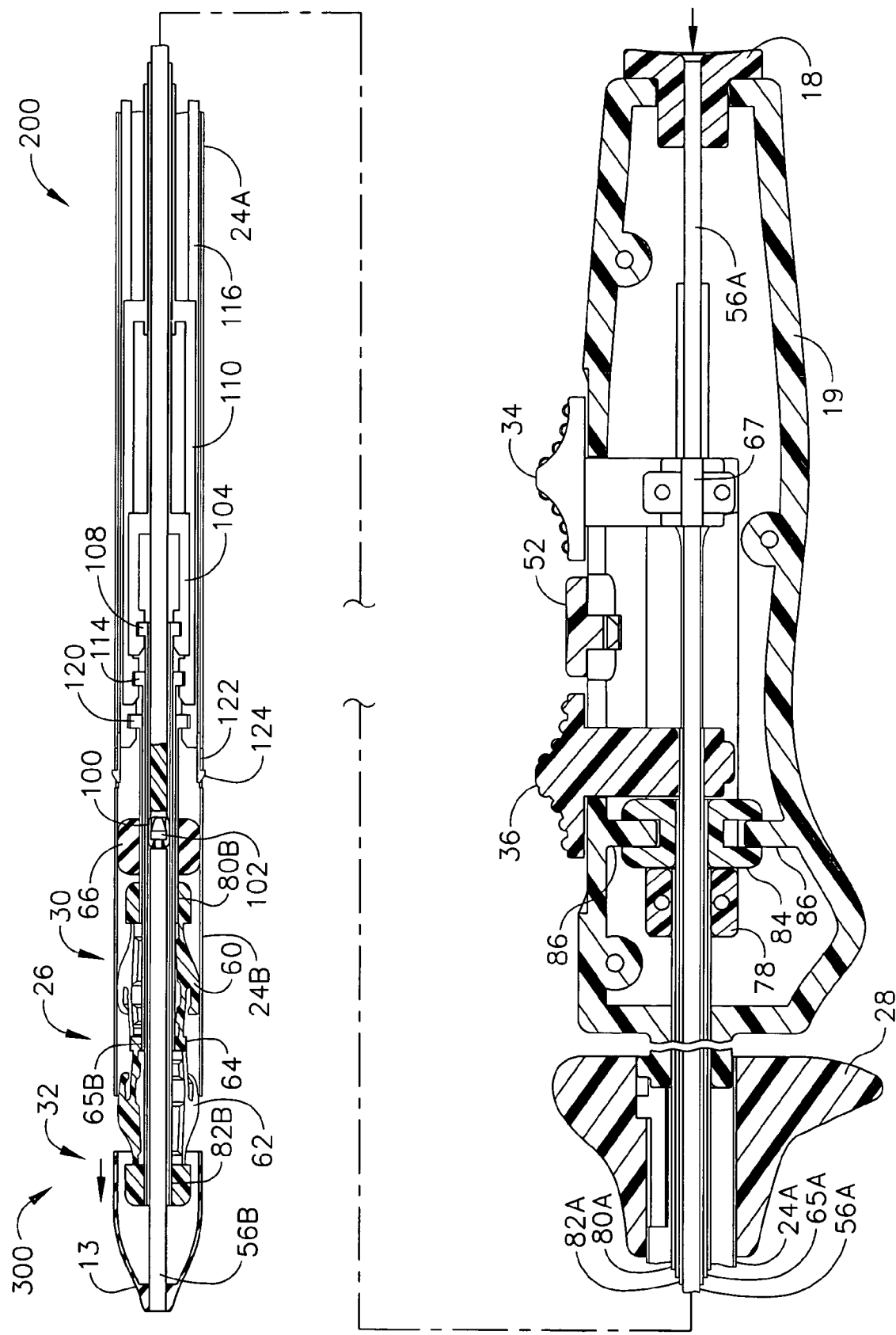
FIG. 14 is a partial cross-sectional view of the device of FIG. 1, shown with the tip extended.

To prevent inadvertent deployment of ring deployment mechanism 26, applier 10 of the present example is provided with a locking element 52. In the present example, locking element 52 is operable to move from a locked position to an unlocked position. In FIGS. 1, 5, 6, 10, 13-15, and 19, locking element 52 is shown in a locked position preventing actuating movement of first actuator 34 and second actuator 36. In FIGS. 7, 8, and 15, locking element 52 is shown in the unlocked position, allowing actuators 34, 36 to move to the actuated position. In the present example, locking element 52 is resiliently urged to the locked position, and may be placed in the unlocked position by the exertion of a downward force on locking element 52. Of course, locking element 52 need not necessarily take the form of the locking element 52 depicted in the figures (i.e., that of a button), and any suitable mechanism or structure may be used to provide a locking element 52. It will also be appreciated that locking element 52 may be eliminated or supplemented.

Figure 12:
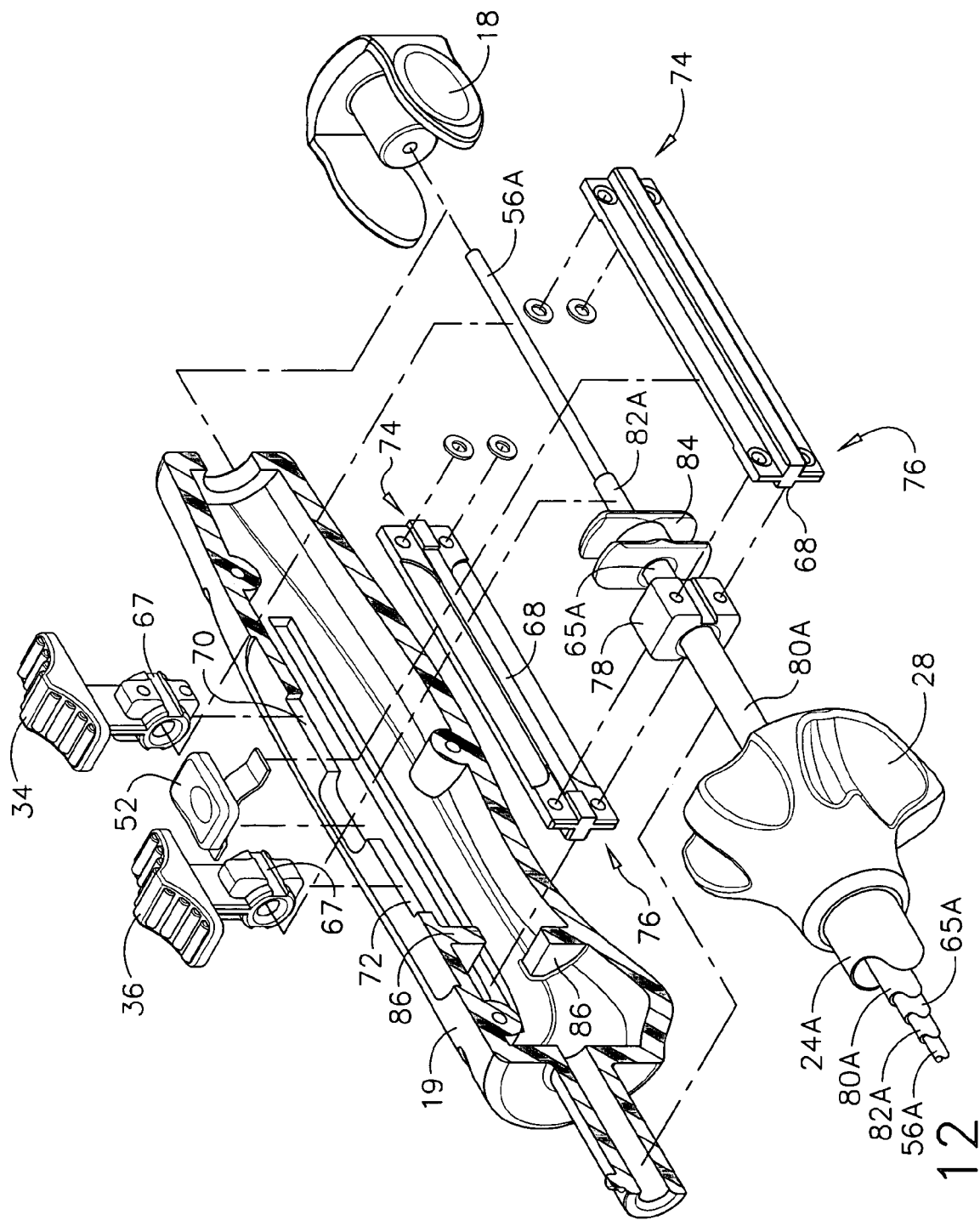
FIG. 12 is a cross-sectional view of a proximal portion of the device of FIG. 1.

As stated above, first deployment actuator 34 of the present example is operable to control proximal fingers 60 and second deployment actuator 36 is operable to control distal fingers 62. As shown in FIG. 12, first and second ring deployment actuators 34, 36 each comprise a pair of grooves 67 that are configured to slide on a track 68 of handle 19. The range of first actuator 34 is limited by the width of a slot 70, while the range of second actuator 36 is limited by the width of a slot 72. As mentioned above, locking element 52 may be utilized to prevent inadvertent movement of first or second actuators 34, 36 within slots 70, 72, respectively.

Figure 22:
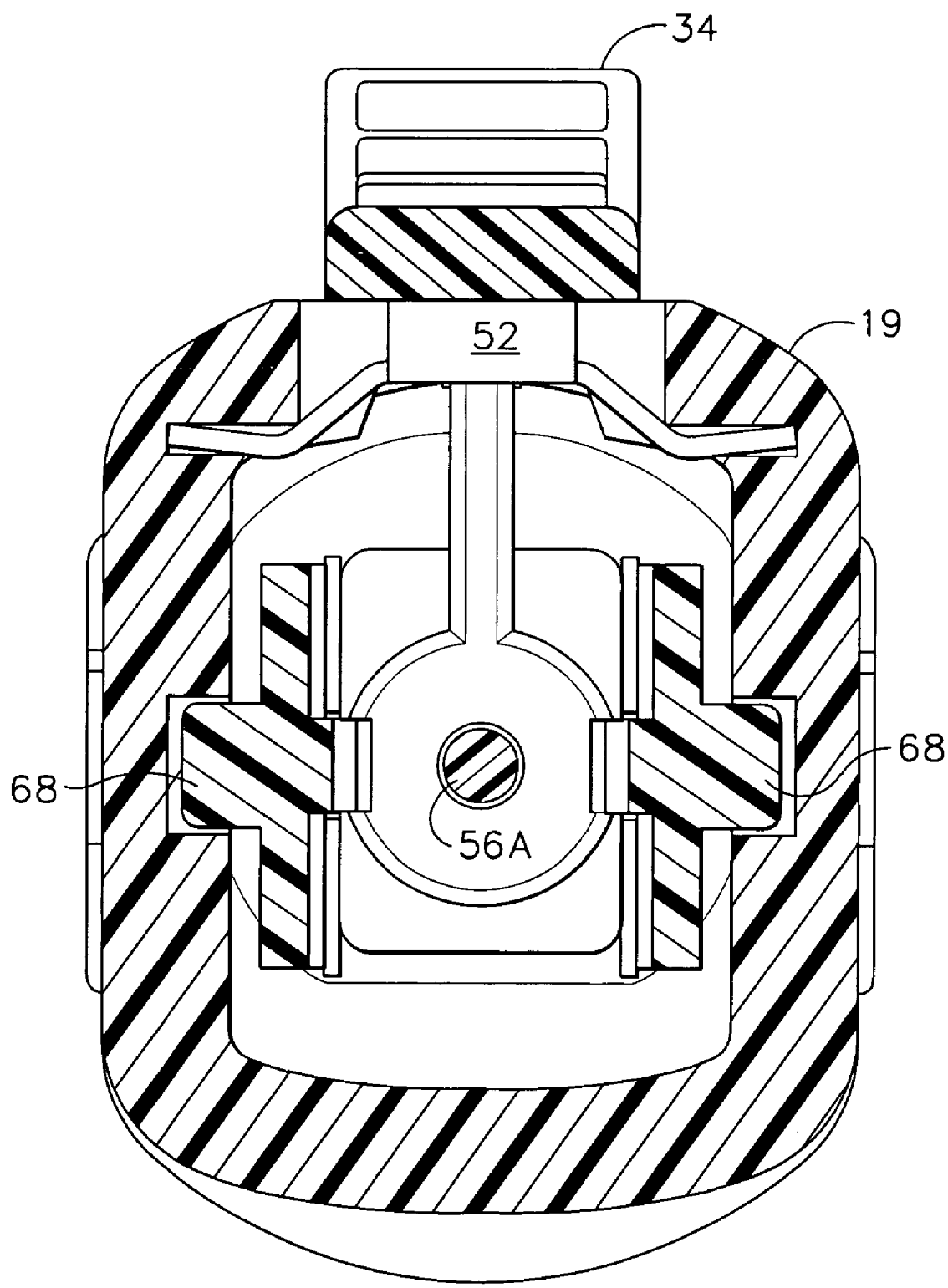
FIG. 22 is a cross-sectional view taken at Plane 22 of the device of FIG. 13.

In the present example, with reference to FIGS. 12 and 22, first actuator 34 is fixedly attached to a proximal portion 74 of track 68. Track 68 is slideable within handle 19. A distal portion 76 of track 68 is fixedly attached to a slider 78, which is slideably engaged with handle 19. Slider 78 is fixedly connected to proximal outer tube portion 80A. Longitudinal motion of first actuator 34 is thereby operable to cause corresponding longitudinal motion of track 68, slider 78, and proximal outer tube portion 80A. Proximal outer tube portion 80A is operable to communicate motion to proximal fingers 60, as will be described below. Other suitable relationships between these components, as well as alternative components, will be apparent to those of ordinary skill in the art.

Figure 21:
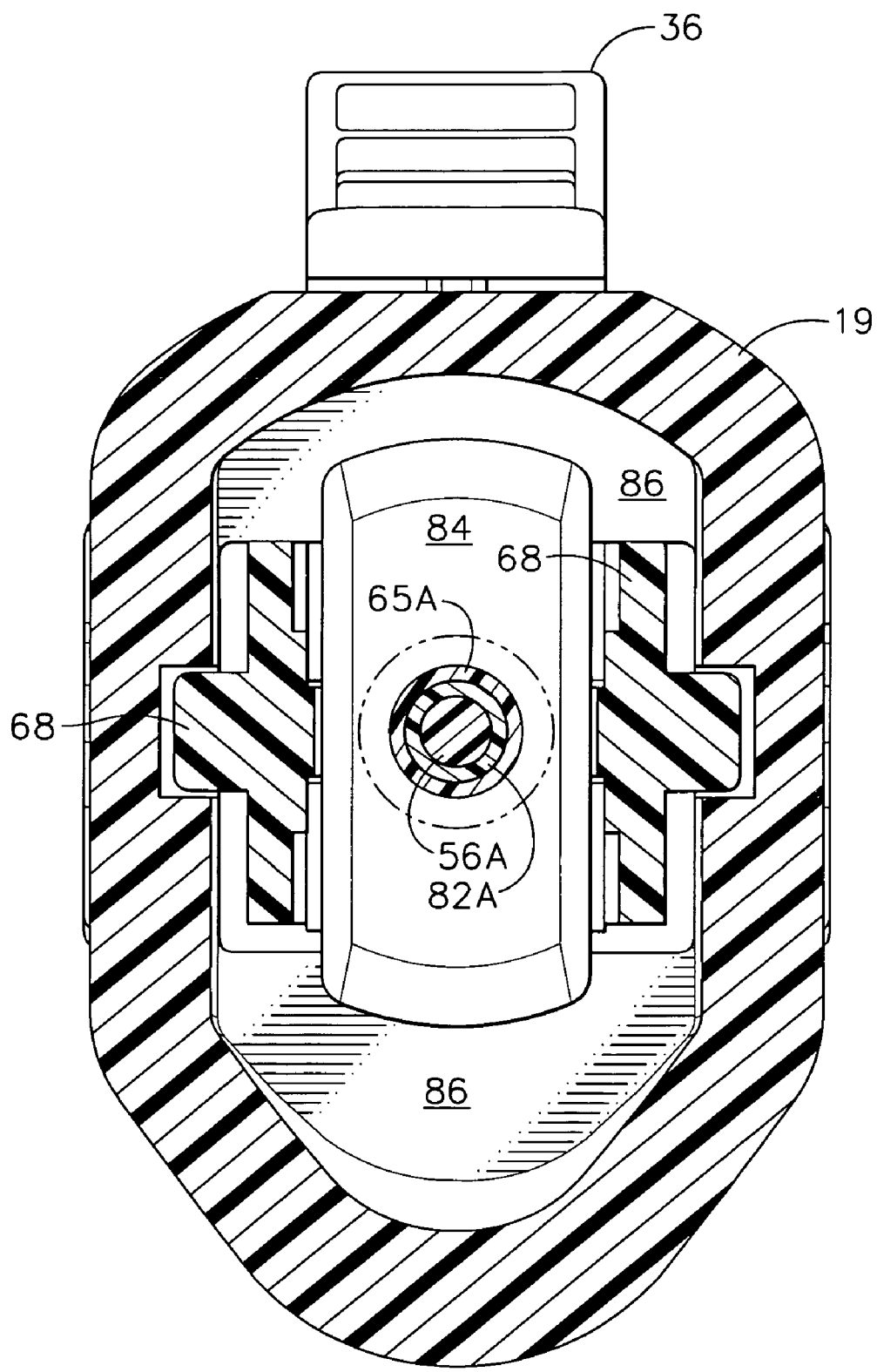
FIG. 21 is a cross-sectional view taken at Plane 21 of the device of FIG. 13.

Referring to FIGS. 12 and 21, the proximal end of a proximal ground tube portion 65A is fixedly attached to an anchor member 84. Anchor member 84 is configured to engage with bosses 86, which are integral with handle 19. Accordingly, in the present example, anchor member 84 and bosses 86 are configured to prevent relative longitudinal movement between proximal ground tube portion 65A and handle 19. Of course, any other configuration may be used.

In the present example, second actuator 36 is fixedly secured to a proximal inner tube portion 82A. Proximal inner tube portion 82A extends longitudinally through proximal ground tube portion 65A. Proximal inner tube portion 82A is operable to communicate motion to distal fingers 62, as will be described below. Other suitable relationships between these components, as well as alternative components, will be apparent to those of ordinary skill in the art.

Accordingly, in this example, it will be appreciated that first actuator 34 controls actuation of proximal fingers 60, and second actuator 36 controls actuation of distal fingers 62. It should be noted that although second actuator 36 is configured to slide on track 68 in the present example, second actuator 36 is not statically attached to track 68. Therefore, longitudinal movement of track 68 caused by motion of first actuator 34 does not cause longitudinal movement of second actuator 36. Of course, handle 19 and components thereof may be configured in any other suitable way. By way of example only, first actuator 34 may be configured to control actuation of distal fingers 62, and second actuator 36 may be configured to control actuation of proximal fingers 60. Still other suitable alternative configurations will be apparent to those of ordinary skill in the art.

In the present example, a proximal tip tube portion 56A is fixedly secured to tip actuator 18. Tip actuator 18 is slideably engaged with handle 19. The proximal end of proximal tip tube portion 56A is fixedly secured to tip actuator 18. A clip 100 is positioned at the distal end of proximal tip tube portion 56A. The distal end of a distal tip tube portion 56B is fixedly secured to tip 13. The proximal end of distal tip tube portion 56B comprises a clip member 102. Clip member 102 and clip 100 are configured to engage, such as by clip member 102 snapping into clip 100, thereby joining proximal tip tube portion 56B and distal tip tube portion 56A. Accordingly, with clip 100 and clip member 102 engaged, tip actuator 18 is operable to move tip 13 from a retracted position to an extended position. Of course, any suitable alternative for joining proximal tip tube portion 56B and distal tip tube portion 56A may be used. In addition, it will be appreciated that any other structure, mechanism, or configuration may be used to effect mechanical communication from tip actuator 18 to tip 13.

Proximal tip tube portion 56A is coaxially positioned within proximal inner tube portion 82A. As previously stated, the proximal end of proximal inner tube portion 82A is fixedly secured to second actuator 36. The distal end of proximal inner tube portion 82A comprises a pair of clip arms 104 extending longitudinally therefrom. Alternatively, any other number of clip arms 104 or clip arm 104 alternatives may be used. In the present example, each clip arm 104 has a recessed portion 106. Applier 10 further comprises a distal inner tube portion 82B, which is coaxially positioned around distal tip tube portion 56B. The distal end of distal inner tube portion 82B is fixedly secured to the distal portion 32 of ring deployment mechanism 26. The proximal end of distal inner tube portion 82B comprises an annular flange 108. Annular flange 108 is sized to fit in recesses 106. In other words, clip arms 104 are configured to engage with annular flange 108. Accordingly, proximal inner tube portion 82A and distal inner tube portion 82B may be selectively joined by engagement of clip arms 104 with annular flange 108. With proximal inner tube portion 82A so joined with distal inner tube portion 82B, second actuator 36 is operable to effect movement of distal portion 32 of ring deployment mechanism 26. Of course, any suitable alternative for joining proximal inner tube portion 82A and distal inner tube portion 82B may be used. In addition, it will be appreciated that any other structure, mechanism, or configuration may be used to effect mechanical communication from second actuator 36 to distal portion 32 of ring deployment mechanism 26.

Proximal inner tube portion 82A is coaxially positioned within proximal ground tube portion 65A. As previously stated, the proximal end of proximal ground tube portion 65A is fixedly secured to anchor member 84, which is engaged with bosses 86 formed in handle. The distal end of proximal ground tube portion 65A comprises a pair of clip arms 110 extending longitudinally therefrom. Alternatively, any other number of clip arms 110 or clip arm 110 alternatives may be used. In the present example, each clip arm 110 has a recessed portion 112. Applier 10 further comprises a distal ground tube portion 65B, which is coaxially positioned around distal inner tube portion 82B. The distal end of distal ground tube portion 65B is fixedly secured to mid-ring 64 of ring deployment mechanism 26. The proximal end of distal ground tube portion 65B comprises an annular flange 114. Annular flange 114 is sized to fit in recesses 112. In other words, clip arms 110 are configured to engage with annular flange 114. Accordingly, proximal ground tube portion 65A and distal ground tube portion 65B may be selectively joined by engagement of clip arms 110 with annular flange 114. With proximal ground tube portion 65A so joined with distal ground tube portion 65B, engagement of anchor member 84 with bosses 86 is operable to prevent longitudinal movement of mid-ring 64 of ring deployment mechanism 26 relative to handle 19. Of course, any suitable alternative for joining proximal ground tube portion 65A and distal ground tube portion 65B may be used. In addition, it will be appreciated that any other structure, mechanism, or configuration may be used to prevent longitudinal movement of mid-ring 64 of ring deployment mechanism 26 relative to handle 19.

Proximal ground tube portion 65A is coaxially positioned within proximal outer tube portion 80A. As previously stated, the proximal end of proximal outer tube portion 80A is fixedly secured to first actuator 34. The distal end of proximal outer tube portion 80A comprises a pair of clip arms 116 extending longitudinally therefrom. Alternatively, any other number of clip arms 116 or clip arm 116 alternatives may be used. In the present example, each clip arm 116 has a recessed portion 118. Applier 10 further comprises a distal outer tube portion 80B, which is coaxially positioned around distal ground tube portion 65B. The distal end of distal outer tube portion 80B is fixedly secured to the proximal portion 30 of ring deployment mechanism 26. The proximal end of distal outer tube portion 80B comprises an annular flange 120. Annular flange 120 is sized to fit in recesses 118. In other words, clip arms 116 are configured to engage with annular flange 120. Accordingly, proximal outer tube portion 80A and distal outer tube portion 80B may be selectively joined by engagement of clip arms 116 with annular flange 120. With proximal outer tube portion 80A so joined with distal outer tube portion 80B, first actuator 34 is operable to effect movement of proximal portion 30 of ring deployment mechanism 26. Of course, any suitable alternative for joining proximal outer tube portion 80A and distal outer tube portion 80B may be used. In addition, it will be appreciated that any other structure, mechanism, or configuration may be used to effect mechanical communication from first actuator 34 to proximal portion 30 of ring deployment mechanism 26.

The proximal end of proximal sheath portion 24A is fixedly secured to sheath actuator 28. The distal end of proximal sheath portion 24A comprises a pair of clip arms 122 extending longitudinally therefrom. Alternatively, any other number of clip arms 122 or clip arm 122 alternatives may be used. In the present example, each clip arm 122 has a protrusion 124 extending outwardly therefrom. The proximal end of distal sheath portion 24B comprises a pair of openings 126 that are sized and spaced to engagingly receive protrusions 124. Accordingly, proximal sheath portion 24A and distal sheath portion 24B may be selectively joined by engagement of protrusions 124 of clip arms 122 with openings 126 in distal sheath portion 24B. With proximal sheath portion 24A and distal sheath portion 24B so joined, sheath actuator 28 is operable to effect movement of distal sheath portion 24B. Of course, any suitable alternative for joining proximal sheath 24A and distal sheath 24B may be used. In addition, it will be appreciated that any other structure, mechanism, or configuration may be used to effect mechanical communication from sheath actuator 28 to distal sheath portion 24B.

In the present example, clip arms 104, 110, and 116 comprise a flexible yet resilient plastic materials. Clip arms 104, 110, and 116 are configured to flex outwardly to engage and disengage with flanges 108, 114, and 120; yet are resiliently urged inwardly in response to such flexing to maintain such engagement. Clip arms 104, 110, and 116 are sufficiently rigid to transfer longitudinal forces to flanges 108, 114, and 120 without substantial bending of clip arms 104, 110, and 116. Alternatively, clip arms 104, 110, and 116 may have any other suitable properties, features, or configurations.

In light of the foregoing, it will be appreciated that applier 10 of the present example may be provided in separate portions—a proximal portion 200 and a distal portion 300. Such portioning or separability may be provided by the selective decoupling of flanges 108, 114, and 120 with clip arms 104, 110, and 116, respectively, as well as the selective decoupling of openings 126 with clip arms 124. In other words, applier 10 may be "broken apart" into a proximal portion 200 and a distal portion 300 by disengagement of the above-mentioned components. With such capability, after applier 10 has been used, the used distal portion 300 may be discarded, and a new distal portion 300 may be joined to the used proximal portion 200. Of course, a used distal portion 300 need not be discarded, and it will be appreciated that an ability to separate distal and proximal portions 300, 200 of an applier 10 may offer a variety of advantages and functions. By way of example only, the separability of portions 300, 200 may permit a modularity of distal portions 300. In other words, a variety of distal portions 300, each distal portion 300 having unique features, functions, advantages, configurations, or capabilities, may be coupled with a proximal portion 200 as desired. Similarly, the same distal portion 300 may be coupled with a variety of proximal portions 200, each proximal portion 200 having unique features, functions, advantages, configurations, or capabilities. Embodiments of such modular variation will be apparent to those of ordinary skill in the art, as will other possibilities provided by having separable portions 200, 300.

Figure 20:
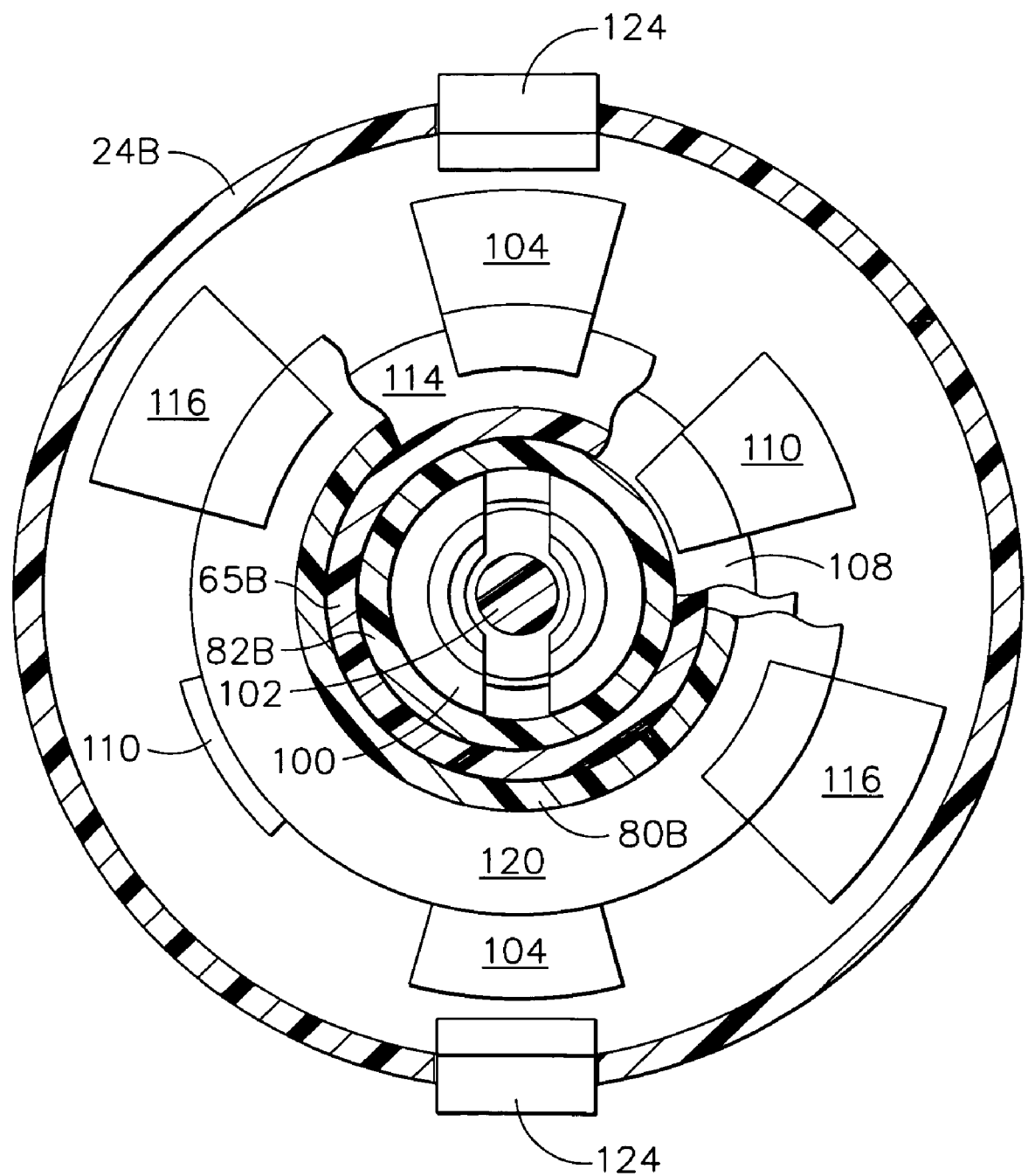
FIG. 20 is a cross-sectional view taken at Plane 20 of the device of FIG. 13.

In the present example, with reference to FIG. 20, clip arms 104, 110, and 116 are sized such that their respective outermost surfaces are positioned adjacent to the inner diameter of sheath 24A, 24B when applier 10 is fully assembled. Similarly, clip 100 is sized such that its outermost surface is positioned adjacent to the inner diameter of distal inner tube portion 82B when applier 10 is fully assembled. It will be appreciated that such a configuration of the foregoing components may reduce the likelihood of inadvertent disengagement of flanges 108, 114, and 120 with clip arms 104, 110, and 116, respectively, as well as inadvertent disengagement of clip 100 with clip member 102. Of course, such prevention may be provided by any other structure or configuration, or may be eliminated altogether.

Figure 10:
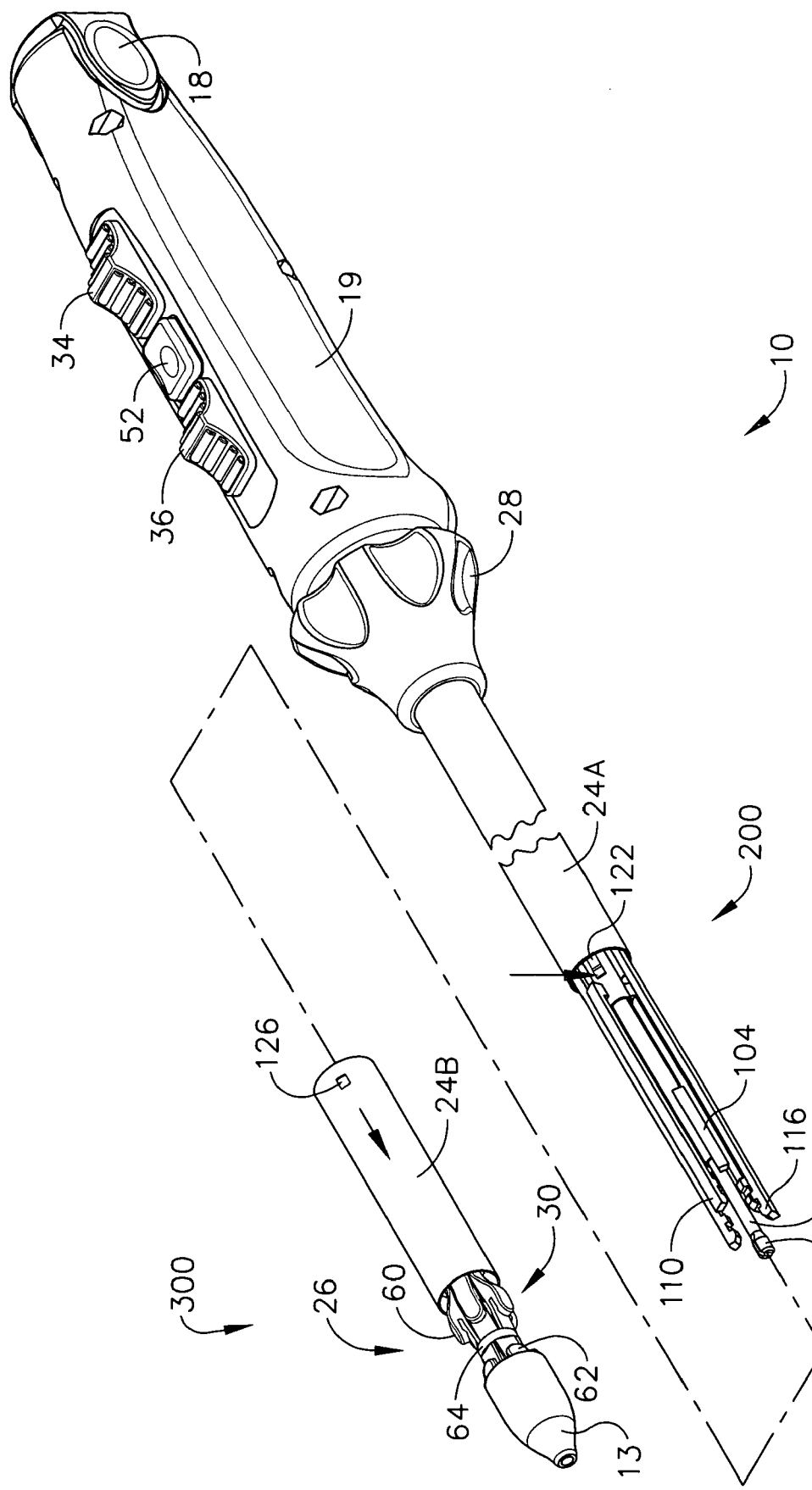
FIG. 10 is a partial exploded view of the device of FIG. 1.
Figure 11:
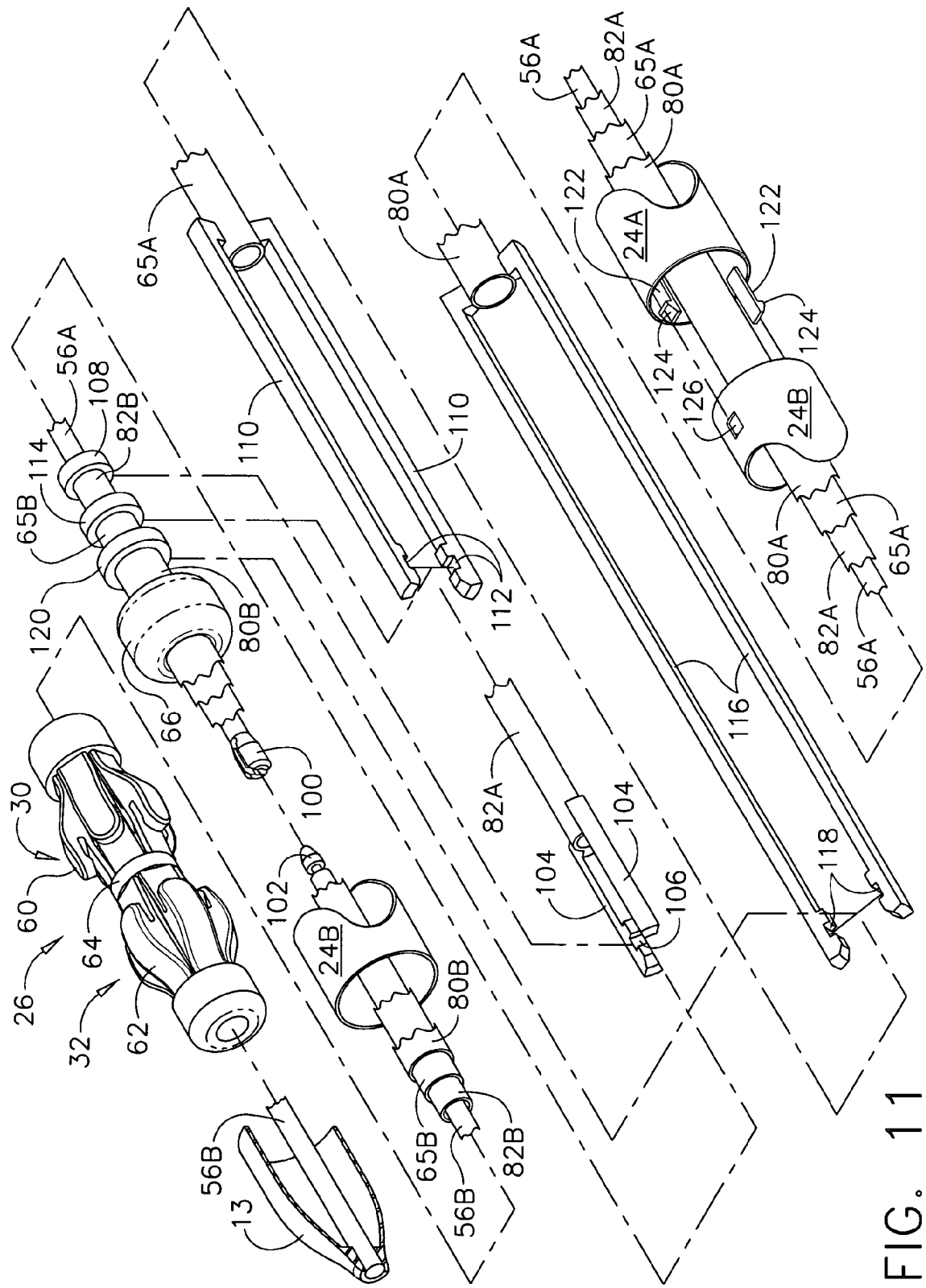
FIG. 11 is an exploded view of an actuation mechanism of the device of FIG. 1.
Figure 19:
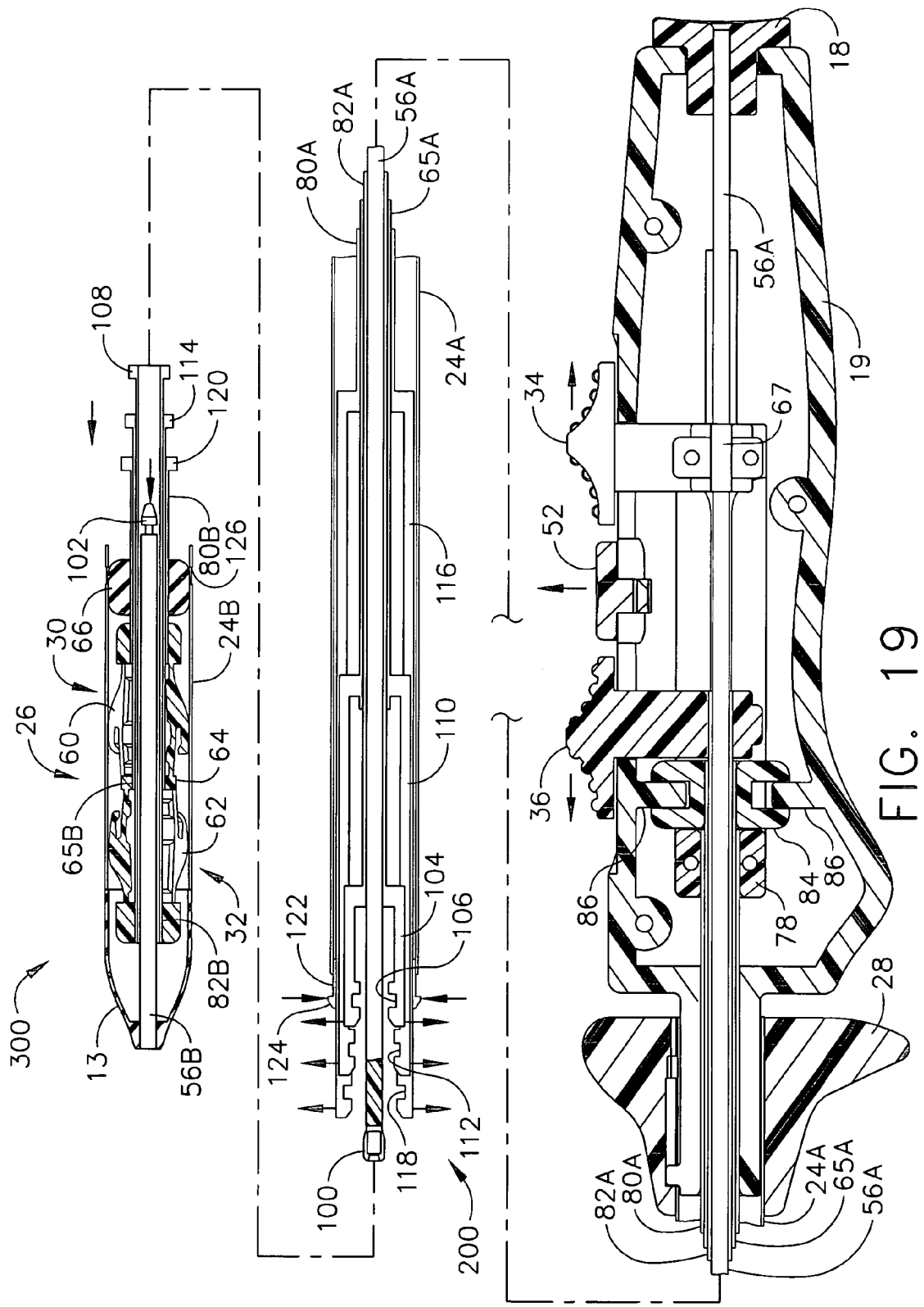
FIG. 19 is a partial cross-sectional view of the device of FIG. 1.

With reference to FIGS. 10 and 19, applier 10 of the present example may be disassembled by disengaging protrusions 124 of clip arms 122 with openings 126 in distal sheath portion 24B. Such disengagement may be effected by depression of protrusions 124 inward while pulling proximal and distal sheath portions 24A. 24B apart. Upon separating sheath portions 24A, 24B, each set of clip arms 116, 110, and 104 may be disengaged from respective annular flanges 120, 114, and 108; and clip 100 may be disengaged from clip member 102. Applier 10 may be reassembled by reversing the above steps. Of course any other procedures may be used to disassemble and/or assemble/reassemble applier 10.

While, in the present example, distal and proximal portions 300, 200 are separable near the distal end of applier 10, it will be appreciated that applier 10 may be configured such that distal and proximal portions 300, 200 are separable at any other longitudinal location or locations along shaft 15 or applier 10. By way of example only, flanges 108, 114, and 120 may be longitudinally positioned as shown (i.e., closer to the distal end of shaft 15 than the proximal end of shaft), such that tubes 56A and 56B, 82A and 82B, 65A and 65B, and 80A and 80B may be coupled and decoupled near the distal end of shaft 15; while the sheath portions 24A and 24B may be configured such that they may be coupled and decoupled near the proximal end of shaft 15. Thus, various portions of distal and proximal portions 300, 200 may couple and decouple at different longitudinal regions of applier 10. Other suitable longitudinal locations for coupling and decoupling distal and proximal portions 300, 200, including but not limited to differing longitudinal locations for coupling and decoupling various portions or components of distal and proximal portions 300, 200, will be apparent to those of ordinary skill in the art.

Figure 5:
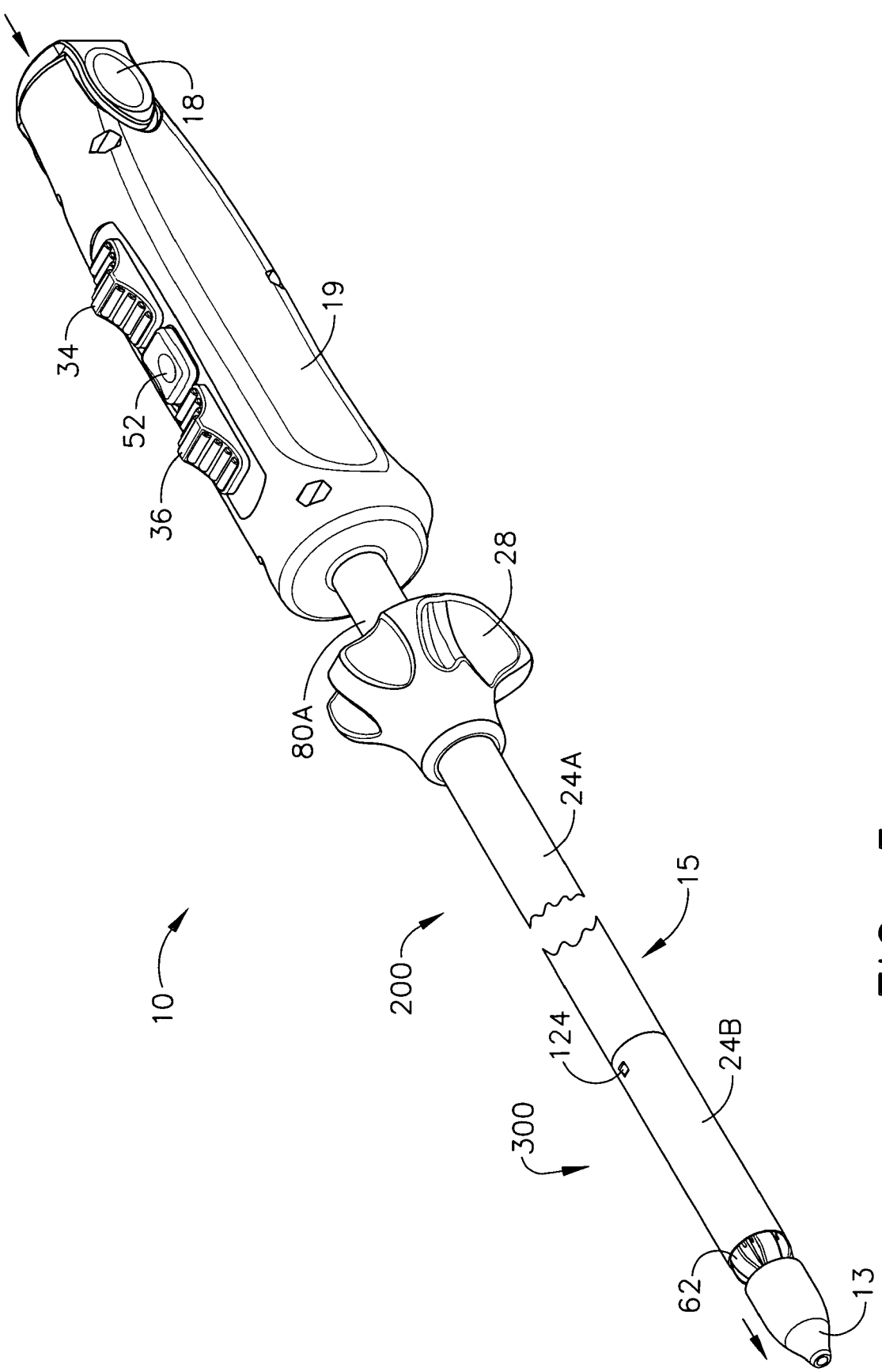
FIG. 5 is a perspective view of the device of FIG. 1, shown with the tip extended.

In use, applier 10 may be inserted adjacent an anastomotic opening in proximate tissue walls 46, 48. Once tip 13 is inserted through the anastomotic opening, tip 13 may be extended using tip actuator 18, thereby exposing a portion of distal fingers 62, as shown in FIGS. 5 and 14. Sheath actuator 28 may be used to retract sheath 24A, 24B to expose ring deployment mechanism 26, as shown in FIGS. 6 and 15. With ring deployment mechanism 26 exposed, locking element 52 may be depressed to permit actuation of deployment actuators 34, 36; and second deployment actuator 36 may be partially actuated to partially actuate distal portion 32 of ring deployment mechanism 26, as shown in FIGS. 7 and 16, thereby effecting partial actuation of the distal portion of anastomotic ring 14. First deployment actuator 34 may be partially actuated to partially actuate proximal portion 30 of ring deployment mechanism 26, as shown in FIGS. 8 and 17, thereby effecting partial actuation of the proximal portion of anastomotic ring 14. First and second deployment actuators 34, 36 may be fully actuated, as shown in FIGS. 9 and 18, to effect full actuation and deployment of anastomotic ring 14. The above steps may be reversed to permit extraction of applier 10 from the anastomosis site. After such use, the distal portion 300 of applier 10 may be removed from the proximal portion 200, and the distal portion 300 disposed of or otherwise dealt with. Another distal portion 300 (or the same distal portion 300) may be attached to the proximal portion 300 for subsequent use.

In another embodiment of use of applier 10, a plurality of distal portions 300 are provided, each being preloaded with a respective anastomotic ring 14. The same proximal portion 200 is successively coupled with each of the distal portions 300 to deploy the anastomotic rings 14 in a single patient. The anastomotic ring 14 deployment steps discussed above are followed with each distal portion 300, with each distal portion 300 being decoupled from the same proximal portion 200 after the anastomotic ring 14 has been deployed from the distal portion 300; and a new distal portion 300 is coupled to the same proximal portion 200 to deploy the next anastomotic ring 14. In this embodiment, each distal portion 300 acts as a reloadable cartridge member for deploying a plurality of anastomotic rings 14. Other variations of use of applier 10 will be apparent to those of ordinary skill in the art.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings. Additional advantages may readily appear to those skilled in the art.

What is claimed is:

1. A surgical instrument for deploying an anastomotic ring device at an anastomosis site, the instrument comprising:

(a) a distal portion, the distal portion comprising a ring deployment mechanism, wherein the ring deployment mechanism is configured to receive and deploy an anastomotic ring;
   (b) a proximal portion in communication with the distal portion, the proximal portion comprising one or more actuation members operable to actuate at least a portion of the ring deployment mechanism; and
   (c) a shaft comprising a distal portion and a proximal portion, wherein the distal portion of the shaft comprises a first plurality of tubes, wherein the proximal portion of the shaft comprises a second plurality of tubes, wherein each tube in the first plurality of tubes in the distal portion of the shaft comprises a flange, wherein each tube in the second plurality of tubes in the proximal portion of the shaft comprises a clip arm configured to selectively engage the flange of a corresponding tube of the first plurality of tubes, wherein the distal portion of the shaft is selectively removable from the proximal portion of the shaft;

wherein the distal portion of the instrument is selectively removable from the proximal portion of the instrument, wherein the distal portion of the instrument and the proximal portion of the instrument are in communication via the shaft.

2. The surgical instrument of claim 1, wherein the plurality of tubes are concentrically aligned.

3. The surgical instrument of claim 1, wherein each tube of the first plurality of tubes is configured to be selectively coupled with a corresponding tube of the second plurality of tubes by respectively engaging the flange of each tube from the first plurality of tubes with the clip arm of a corresponding tube from the second plurality of tubes.

4. The surgical instrument of claim 1, wherein the shaft further comprises a retractable sheath, wherein the sheath is operable to selectively cover at least a portion of the ring deployment mechanism.

5. The surgical instrument of claim 4, wherein the sheath comprises a distal portion and a proximal portion, wherein the distal portion of the sheath is selectively removable from the proximal portion of the sheath.

6. The surgical instrument of claim 1, wherein the distal portion further comprises a tip, wherein the tip is configured to selectively cover at least a portion of the ring deployment mechanism.

7. The surgical instrument of claim 6, wherein the tip is moveable from a retracted position to an extended position via at least one tube.

8. The surgical instrument of claim 3, wherein the clamp arm is configured to transfer at least one longitudinal force to the flange with which it is respectively engaged.

9. The surgical instrument of claim 8, wherein at least one of the one or more actuation members is operable to provide the at least one longitudinal force to the clamp arm.

10. The surgical instrument of claim 9, wherein the flange is configured to communicate the at least one longitudinal force to at least a portion of the ring deployment mechanism.

11. The surgical instrument of claim 10, wherein the ring deployment mechanism is configured to deploy at least a portion of an anastomotic ring in response to the at least one longitudinal force.

12. The surgical instrument of claim 1, wherein the proximal portion comprises a handle, wherein the handle comprises the one or more actuator members.

13. The surgical instrument of claim 1, wherein the ring deployment mechanism comprises a plurality of fingers.

* * * * *